(12) United States Patent
Hughes et al.

(10) Patent No.: US 8,679,008 B2
(45) Date of Patent: Mar. 25, 2014

(54) BIOSENSOR DEVICE AND METHOD

(75) Inventors: Darran Hughes, Ranelagh (IE); Daragh McDonnell, Portmarnock (IE); Phil McDarby, Rialto (IE)

(73) Assignee: Galvanic Limited, Dublin (IE)

( * ) Notice: Subject to any disclaimer, the term of this patent is extended or adjusted under 35 U.S.C. 154(b) by 1625 days.

(21) Appl. No.: 12/070,345

(22) Filed: Feb. 15, 2008

(65) Prior Publication Data

US 2008/0208016 A1 Aug. 28, 2008

Related U.S. Application Data

(60) Provisional application No. 60/901,733, filed on Feb. 16, 2007.

(51) Int. Cl.
*A61B 5/00* (2006.01)
*G06F 19/00* (2011.01)

(52) U.S. Cl.
CPC ..................................... *G06F 19/30* (2013.01)
USPC ......................................................... 600/300

(58) Field of Classification Search
USPC ......................................... 600/300–301, 544
See application file for complete search history.

(56) References Cited

U.S. PATENT DOCUMENTS

| | | | | |
|---|---|---|---|---|
| 3,942,516 | A | 3/1976 | Glynn et al. | 128/2.1 B |
| D243,284 | S | 2/1977 | Myers | D83/1 F |
| 4,354,505 | A | 10/1982 | Shiga | 128/732 |
| 4,683,891 | A | 8/1987 | Cornellier et al. | 128/630 |
| 5,209,494 | A | 5/1993 | Spector | 273/460 |
| 5,720,619 | A | 2/1998 | Fisslinger | 434/336 |
| 6,024,700 | A * | 2/2000 | Nemirovski et al. | 600/300 |
| 6,026,322 | A | 2/2000 | Korenman et al. | 600/547 |
| 6,067,468 | A | 5/2000 | Korenman et al. | 600/547 |
| 6,167,299 | A | 12/2000 | Galchenkov et al. | 600/547 |
| 6,415,176 | B1 * | 7/2002 | Scheirer et al. | 600/547 |
| 6,520,905 | B1 | 2/2003 | Surve et al. | 600/26 |

(Continued)

FOREIGN PATENT DOCUMENTS

| | | | |
|---|---|---|---|
| WO | WO 86/01317 | 2/1986 | G06F 15/42 |
| WO | WO 2005/018442 | 3/2005 | |

(Continued)

OTHER PUBLICATIONS

Mindware Forum: Tiny Biofeedback Game—relax to win Sensor—Developed by Phillips UK for Cell Phones, Mar. 17, 2006, [online] [retrieved Sep. 10, 2008]. Retrieved from the Internet <URL: http://www.bruceeisner.com/mindware/2006/03/tiny_biofeedbac.html>.

*Primary Examiner* — Bill Thomson
*Assistant Examiner* — Bobby Soriano
(74) *Attorney, Agent, or Firm* — K&L Gates LLP

(57) ABSTRACT

In part, one aspect of the invention relates to a portable, handheld biosensor device that is held between two fingers of the same hand or otherwise contacts two points on a user's skin. The sensor device includes a pair of conductive or semi-conductive electrodes and associated circuitry designed to sense, amplify and digitize the electrical conductance of the skin between the electrodes. The device can additionally be configured to sense additional biometrics from the fingers, including blood oxygenation and skin temperature. Digitized biometric values are transmitted wirelessly (or via direct wire connection, such as a USB cable) to a computing device where the data is utilized to generate a control parameter in a software application whose purpose is to provide anxiety biofeedback or entertainment.

10 Claims, 18 Drawing Sheets

(56) References Cited

U.S. PATENT DOCUMENTS

| | | | |
|---|---|---|---|
| 6,526,315 B1* | 2/2003 | Inagawa et al. | 600/547 |
| 6,751,499 B2* | 6/2004 | Lange et al. | 600/544 |
| 7,467,010 B2* | 12/2008 | Kuramori et al. | 600/546 |
| 7,547,279 B2* | 6/2009 | Kim et al. | 600/300 |
| 7,774,052 B2* | 8/2010 | Burton et al. | 600/544 |
| 2002/0128567 A1* | 9/2002 | Lange et al. | 600/544 |
| 2002/0138018 A1* | 9/2002 | Lange et al. | 600/544 |
| 2003/0093784 A1* | 5/2003 | Dimitrova et al. | 725/10 |
| 2003/0139654 A1* | 7/2003 | Kim et al. | 600/300 |
| 2003/0236451 A1* | 12/2003 | El-Nokaly et al. | 600/300 |
| 2004/0019292 A1* | 1/2004 | Drinan et al. | 600/547 |
| 2004/0117212 A1 | 6/2004 | Kong et al. | |
| 2004/0193068 A1* | 9/2004 | Burton et al. | 600/544 |
| 2005/0137503 A1 | 6/2005 | Hori et al. | |
| 2005/0197590 A1* | 9/2005 | Osorio et al. | 600/544 |
| 2005/0273017 A1* | 12/2005 | Gordon | 600/544 |
| 2006/0052720 A1* | 3/2006 | Ross et al. | 600/554 |
| 2007/0050715 A1* | 3/2007 | Behar | 715/706 |
| 2007/0053513 A1* | 3/2007 | Hoffberg | 380/201 |
| 2007/0066874 A1* | 3/2007 | Cook | 600/300 |
| 2007/0173705 A1* | 7/2007 | Teller et al. | 600/300 |
| 2007/0299322 A1* | 12/2007 | Miyajima et al. | 600/301 |
| 2008/0013747 A1* | 1/2008 | Tran | 381/67 |
| 2008/0214903 A1 | 9/2008 | Orbach | |
| 2008/0215973 A1* | 9/2008 | Zalewski et al. | 715/706 |
| 2010/0076273 A1* | 3/2010 | Shigetou | 600/300 |

FOREIGN PATENT DOCUMENTS

| | | |
|---|---|---|
| WO | WO 2005/110238 A | 11/2005 |
| WO | WO 2007/017263 A | 2/2007 |
| WO | WO 2008/099288 | 8/2008 |

\* cited by examiner

BIOSENSOR DEVICE AND METHOD

RELATED APPLICATIONS

This application claims priority to U.S. Provisional Patent Application Ser. No. 60/901,733 filed on Feb. 16, 2007, the disclosure of which is herein incorporated by reference in its entirety.

FIELD OF INVENTION

The invention relates generally to biometric devices, more specifically to methods and devices for biofeedback suitable for use in stress management and entertainment applications.

BACKGROUND

The measurement and analysis of biological signals and investigation of their correlation with psychological processes has a long history. From the pioneering research into electrodermal phenomena in the late $19^{th}$ century through to widespread application in psychiatry and criminology in the 1950's, the apparatus, methods and theories advanced to the point where practitioners employed instruments such as polygraphs and oscilloscopes as standard tools for evaluation of an individual's psychological state.

In the 1960's the theory and practice of biofeedback via physiological signals, such as electrodermal activity, became a popular field of research. Biofeedback is the process of making a person aware of psychophysical information which they can use to bring processes which are mainly subject to unconscious regulation under their direct (conscious) control. This research emerged from the laboratory and into the marketplace, in the form of commercially available products that people could use as psychological tools for therapy in their own homes.

Early biofeedback devices were relatively simple, the feedback signal typically being represented by the position of an oscilloscope dot on a screen or the pitch of an audio tone. Advances in the processing and graphical capabilities of home computers meant that, by the early 1980's, the feedback provided to the user could be presented in a much richer context for use both in therapeutic and consumer products.

Recently, the use of biofeedback devices in both clinical and commercial settings has increased, finding widespread application in therapies for anxiety, sleep disorders and attention-deficit hyperactivity disorder (ADHD), among others. Several biofeedback products for stress management have also come to market. Reducing the stress associated with modern, urban living is important to the general health of society; hence these products have a useful role to play in helping people to monitor and enhance their mental and physical well-being.

Traditional biofeedback systems are typically attached to the user via tape or some sort of binding. Further, traditional systems are large, heavy, non-portable wired arrangements that do not provide the user with a rewarding experience or desire for repeated use. Additionally, due to variations in human physiology, biometric signals can be difficult to accurately measure and track across the population, making it difficult to provide useful biofeedback on an individual basis. There is a need in the art for a mobile, ergonomic, aesthetically pleasing, entertaining and accurate biofeedback system that provides a user with an effective method for reducing stress and its associated, harmful effects on the body.

SUMMARY OF THE INVENTION

In part, one aspect of the present invention provides an ergonomic biosensor that is aesthetically pleasing and easy to use in everyday settings by the average user. The way in which the user physically interacts with the sensor is a significant advantage of the device. For example, the device is wireless and can be sized to fit between a user's thumb and forefinger. One embodiment of the invention includes a housing with first and second surfaces, the surfaces being electrodes suitable for detecting biometric signals. As described above, the housing is ergonomically designed to be comfortable and easy to hold when the fingertips of one hand (the thumb and one other finger) are placed on the first and second conductive surfaces.

In another aspect, the invention relates to a biometric apparatus. The apparatus includes a housing having a first surface; a second surface adapted to detect an electrodermal signal and an element, such as a processing or filter element, in electrical communication with the second surface and disposed within the housing, the element adapted to filter the electrodermal signal.

In one embodiment of the apparatus, the first surface and the second surface are the same. In another embodiment, each of the first and second surfaces is a conducting electrode. The electrodermal signal can include a first frequency component and a second frequency component. The first frequency component can include an electrodermal level. The second frequency component can include an electrodermal response. The apparatus can further include a transmitter disposed within the housing, the transmitter adapted to transmit the electrodermal signal. In one embodiment, the processing element is a digital signal processor. A portion of the housing can be substantially teardrop, rounded, spherical, cylindrical, angular, regular, and/or irregular in shape.

In yet another aspect, the invention relates to method of measuring a biometric parameter. The method includes the steps of receiving a signal, the signal comprising an electrodermal level portion and an electrodermal response portion; and filtering the electrodermal level portion from the signal. In one embodiment, the filtering step is performed substantially continuously using an adaptive process. The method can further include the step of generating inputs for a controllable system. In addition, the controllable system is selected from a game, a toy, a simulated entity, a remote control, a computing device with a visual display, a portable device, a handheld device, a game console and a home entertainment system.

In still another aspect, the invention relates to a biometric apparatus. The apparatus includes a first electrode and a second electrode, the first and second electrodes sufficiently conductive or otherwise adapted to receive a signal from dermal tissue; an amplifier in electrical communication with at least one electrode, the amplifier adapted to receive the signal and transmit an amplified signal having a first signal portion and a second signal portion; a filter in electrical communication with the amplifier, the filter adapted to receive the amplified signal and transmit the first signal portion; a processor, the processor in electrical communication with the filter and the amplifier, the processor adapted to generate a processed signal in response to the first signal portion; and a transmitter, the transmitter adapted to transmit data in response to the processed signal. In one embodiment, the filter, amplifier, and electrodes operate in the analog domain. In one embodiment, the apparatus also includes at least one converter in electrical communication with the processor, the converter adapted to convert analog signals to digital signals before reaching the processor. The transmitter is a wireless transmitter in one embodiment.

In still yet another aspect, the invention relates to method of performing adaptive biometric measurement. The method includes the steps of continuously (or periodically) monitoring a user's skin for a usage period; receiving data from the user's skin during the usage period; and identifying relative stress trends relating to a user's anxiety level, the relative stress trends determined in response to an anxiety level of the user. The method can further include the step of resetting a counter when the user has maintained the anxiety level for a predetermined period of time. The method can further include the step of controlling an entertainment or self-help program using changes in the stress trends. The entertainment or self-help program can be a game. Also, the entertainment or self-help program can include the simultaneous participation of multiple users on a computing device or on a network of computing devices.

In one embodiment, the user exhibits a similar trend in his/her individual anxiety level in order to co-operatively attain a pre-specified goal. In another embodiment, changes in the user's anxiety level over time can determine one or more properties of an autonomous agent, the well-being of the autonomous agent dependent upon the user's anxiety level. The autonomous agent can be a toy. The autonomous agent can be computer generated. The autonomous agent can be a virtual pet requiring requires the user to "feed" it with relaxation at regular intervals, in order to keep it alive.

In one embodiment, the length of the longest dimension of the biometric device can range from about 1 cm to about 6 cm. In a preferred embodiment, the longest dimension of the device can range from about 3 cm to about 5 cm. In one particular preferred embodiment, the length of the device is about 5 cm and the width is about 3 cm. The weight of the device can range from about 10 g to about 50 g. In another embodiment, the housing has a tear-drop shaped configuration, and can be formed by one or more shells or housing surfaces. Yet another embodiment incorporates a wireless transceiver within the housing.

An aspect of the invention is that, within a single housing, it is capable of incorporating, either individually or simultaneously, electronic circuits for the real-time transduction, conditioning, digitizing and transmission of biophysical data including, but not limited to, a galvanometer, a pulse oximeter and a thermocouple.

Another aspect of the invention is the inclusion of electronic circuitry disposed within the housing and substantially optimized to extract a measure of the user's stress level via their electrodermal activity ("EDA"). The circuitry automatically adapts to filter the electrodermal level ("EDL") from the electrodermal signal, thus allowing the electrodermal response ("EDR") to be amplified to a greater resolution. Since the EDL varies widely between individuals, and the EDR is the primary signal of interest, removing the EDL facilitates the processing of a broad range of skin types via the same procedure. Further, certain embodiments of the invention extract anxiety levels from the electrodermal signal via a continuously adapting measurement rather than the extraction of specific EDR events.

A further aspect of the invention is the generation of inputs for a controllable system, which may include a game, toy, computer, portable/handheld device or home entertainment system. An embodiment of the device can form part of a continuously adaptive feedback loop in which the controllable system can adapt the parameters of the device in response to variations in the user's biometric signal and/or the features extracted there from. The digital signal processing used to extract features from the user's biometric data can be carried out on the device. In yet another embodiment of the device, the digital signal processing can be carried out by the controllable system. The controllable system and the device can exchange data via a wireless link.

In another aspect, the invention relates to a portable biometric apparatus. The apparatus includes a housing having a first surface; a sensing element to transduce a biometric signal; and electronic circuitry disposed within the housing, the circuitry adapted to amplify, filter and digitize the transduced signal. The sensing element can transduce an electrodermal signal. In one embodiment, the housing has second and third surfaces. The sensing element can comprise the second and third surfaces. In one embodiment, the second and third surfaces are positioned relative to the first surface so as to be touched at the same time respectively by the tip of the thumb and one other finger tip of the same hand of a user.

In one embodiment, the first and second surfaces can be positioned ergonomically, so as to be held comfortably by the user. The first and second surfaces can be positioned in parallel on opposite sides of the housing so as to be held comfortably between tip of thumb and tip of forefinger. In one embodiment, the sensing element is adapted to transduce one or both of oxygen saturation of blood hemoglobin, skin temperature. The apparatus can further include a transmitter disposed within the housing, the transmitter adapted to transmit the digitized signal. The transmitter can be a wireless or a wired transmitter. The wireless transmitter can be selected from the group of IR and RF transmitters.

In another aspect, the invention relates to a biometric system. The system includes a client device. The client device can include a client receiver, capable of receiving data from a biometric apparatus transmitter; and a client processor in communication with the client receiver, the client processor executing a client application program, the client application program utilizing data received from the biometric apparatus. The system can further include a biometric apparatus receiver in communication with the biometric apparatus processor and a client transmitter in communication with the client processor, the client transmitter transmitting control information from the client processor to the biometric apparatus receiver. In one embodiment, the client processor includes a digital signal analyzer, the digital signal analyzer in communication with the client receiver.

In yet another embodiment, the client processor further includes a client application processor in communication with the digital signal analyzer; and an interactive visualization engine in communication with the client application processor. In one embodiment, the system is a closed, adaptive, feedback loop in which the client application utilizes the output of the digital signal analyzer to adapt the electrical characteristics of the biometric apparatus, in order to achieve optimal sensing of the biometric signal. With respect to the system, in one embodiment, the client processor is a game console, a toy, a computer, a portable device, a handheld device or a home entertainment system.

In another aspect, the invention relates to a portable biometric apparatus. The apparatus includes a housing, the housing comprising an insulator material; a power source disposed within the housing; a first electromagnetic wave transmitting surface disposed proximate to the housing; a first electromagnetic wave receiving surface disposed proximate to the housing, the first receiving surface insulated from the first transmitting surface by a portion of the housing; and a sensing element disposed within the housing and in electrical communication with the power source and both the first electromagnetic wave receiving surface and the first electro-magnetic wave transmitting surface. The first wave transmitting surface can be a surface electrode and the first wave receiving surface can be a surface electrode. The first wave transmitting surface can include a light source and the first wave receiving surface can include a photodetector. The first wave receiving surface can include a temperature sensor. In one embodiment, the first wave transmitting surface transmits an electrodermal signal to the sensing element when in contact with skin.

In another aspect, the invention relates to a biometric sensor. The biometric sensor includes an ergonomically shaped device housing, the housing shaped to fit between a first digit and a second digit of a user's hand; a first sensor surface disposed proximate to the housing to contact the first digit; a second sensor surface disposed proximate to the housing to contact the second digit; and a signal receiving element disposed within the housing and in electrical communication with the first sensor surface and the second sensor surface, and the signal receiving element designed to sense a physiological characteristic of the user. In one embodiment, the first digit is a thumb and the second digit is a forefinger. The sensor surfaces can be disposed on opposite faces of the housing. The sensor surfaces can be substantially parallel and face away from each other. The housing can have a substantially teardrop shape. The biometric sensor can further include a circuit that either amplifies, filters or digitizes a received biometric signal. The longest dimension of the housing can range from 1 cm about to about 6 cm.

In another aspect, the invention relates to a biometric apparatus. The apparatus includes a first electrode and a second electrode, the first and second electrodes sufficiently conductive to transduce electrodermal activity, the first electrode and the second electrode disposed proximate to a housing; an amplifier in electrical communication with the first and second electrodes, the amplifier adapted to amplify a transduced signal; a converter in electrical communication with the amplifier, wherein the converter converts analog signals to digital signals; a processor, the processor in electrical communication with the converter, the processor capable of controlling a flow of digitized data, the processor disposed within the housing; and a transmitter, the transmitter adapted to transmit data generated by the processor.

In one embodiment, the transmitter can be a wireless transmitter. The biometric apparatus can further include a filter that passes more of a phasic component of the electrodermal signal than a tonic component of the electrodermal signal. The processor can be programmed to track variations in the tonic component of an electrodermal signal over time. The apparatus can further include a detector element in communication with the processor. In one embodiment, the detector element is selected from the group consisting of a photodetector, a thermocouple, a temperature sensor, and a blood oxygen level sensor. The data can be transmitted to a client computing device including, but not limited to a personal computer, a handheld device, a mobile phone, a home entertainment system, a game console, wherein the client device performs the majority of the processing of the user data and audiovisual presentation to the user.

In another aspect, the invention relates to a method of determining the anxiety level of a user from an electrodermal signal. The method includes the steps of receiving electrodermal data from the user; filtering the data to remove high frequency components; calculating the slope of the filtered data; thresholding the filtered data; accumulating a number of events within a threshold value; and determining a number of accumulated events for a given time period. The method can further include the step of generating inputs for a controllable system in response to the number of events. The high frequency components can correspond to an electrodermal response.

Various embodiments and aspects of the invention relate to embodiments involving a plurality of biometric sensors used in a group context.

In another aspect, the invention relates to a software application in communication with two or more biosensors connected to a group of users in which each user is given audiovisual feedback that is correlated with an aggregate biometric property of the group. The software application can support two or more users ("the group"), each user's biosignals being sensed by one or more biosensors. The output of each biosensor can contribute to a value representative of an aggregate biological property of the group. The application can run on multiple computing devices, each instance of the application being in communication with one or more biosensors. One or more presentation devices can provide a representation to the group, the representation being correlated with an aggregated metric extracted from each user's biometric data. In one embodiment, the visual representation is an animation, the state of the animation being determined by the aggregated metric.

In another embodiment, the biometric apparatus can transduce one or more of the following physiological processes, electrodermal activity, oxygen saturation of blood hemoglobin, skin temperature, brain electrical activity, heart electrical activity, muscle electrical activity. The common representation can be an animation. In one embodiment, the application provides a representation of an aspect of the group's state, as extracted from an aggregate of the group's biometric data. The representation can reflect the combined stress/relaxation level of the group. The stress/relaxation level can be extracted on a per user basis and mapped to a scalar number in a predefined range. Further, the scalar number can be in the range 0 to 100, with 0 representing the least stressed and 100 representing the most stressed. In one embodiment, the group relaxation level is the summation of the individual relaxation levels. The group relaxation level can be the minimum of the individual users within the group. Further, the group relaxation level can be taken to be maximum of the individual users within the group. In another embodiment, the group relaxation level is a function of the individual users' relaxation levels over time.

In one embodiment, the application is an embodiment of a massively multiplayer, online virtual world, where players in the virtual environment can relax together to achieve a collaborative objective within the environment. The application can part of a group anxiety management system in the mental healthcare field. The application can be a relaxation/team-building tool for use in a corporate setting. The application can be a tool for promoting relaxation and cooperation in an educational setting, including a school or university class room.

Various embodiments and aspects of the invention relate to embodiments involving artificial intelligence and virtual pets controlled by biometric signals.

In another aspect, the invention relates to a system that includes a virtual agent application in communication with a biosensor. The system has the following components: a biosensor that transduces a physiological parameter from a persons body, a software application that executes on a client device CPU which has a communication link with the biosensor device, a signal processing component within the application which can perform digital analysis of the biometric data stream and extract a metric of the users' psychological state from the data stream, a virtual agent simulation component within the application that receives input from the signal processing unit, an animation manager component that manages the update of the visual representation of the virtual agent, and a visual display component that presents the animation of the virtual agent to the user.

The virtual agent can be a simulated virtual creature which has internal drives requiring it to interface with the user via the biosensor at regular intervals. The internal state of the creature is stored in memory that persists between user sessions. In one embodiment, the creature has an internal drive that is equivalent to hunger which drives it to require "feeding" by the user, via the biosensor. The state of the virtual creature is modified by the user's biometric "feeding" and over time the wellbeing of the virtual creature reflects the regularity of these feeding sessions. In one embodiment, the client device can be a personal computer, a mobile phone, a PDA, a game console, a set top box, a home entertainment system.

Further, the client device can include the biometric sensor and graphical display device within a unitary housing. The agent can possess the ability to transfer its state between different client devices, for example, from a mobile device to a PC. The virtual agent can be embodied in a robotic device whose behavior reflects its internal state, including its hunger for biometric input.

BRIEF DESCRIPTION OF THE DRAWINGS

These embodiments and other aspects of this invention will be readily apparent from the detailed description below and the appended drawings, which are meant to illustrate and not to limit the invention, and in which.

DETAILED DESCRIPTION

Figure 1:
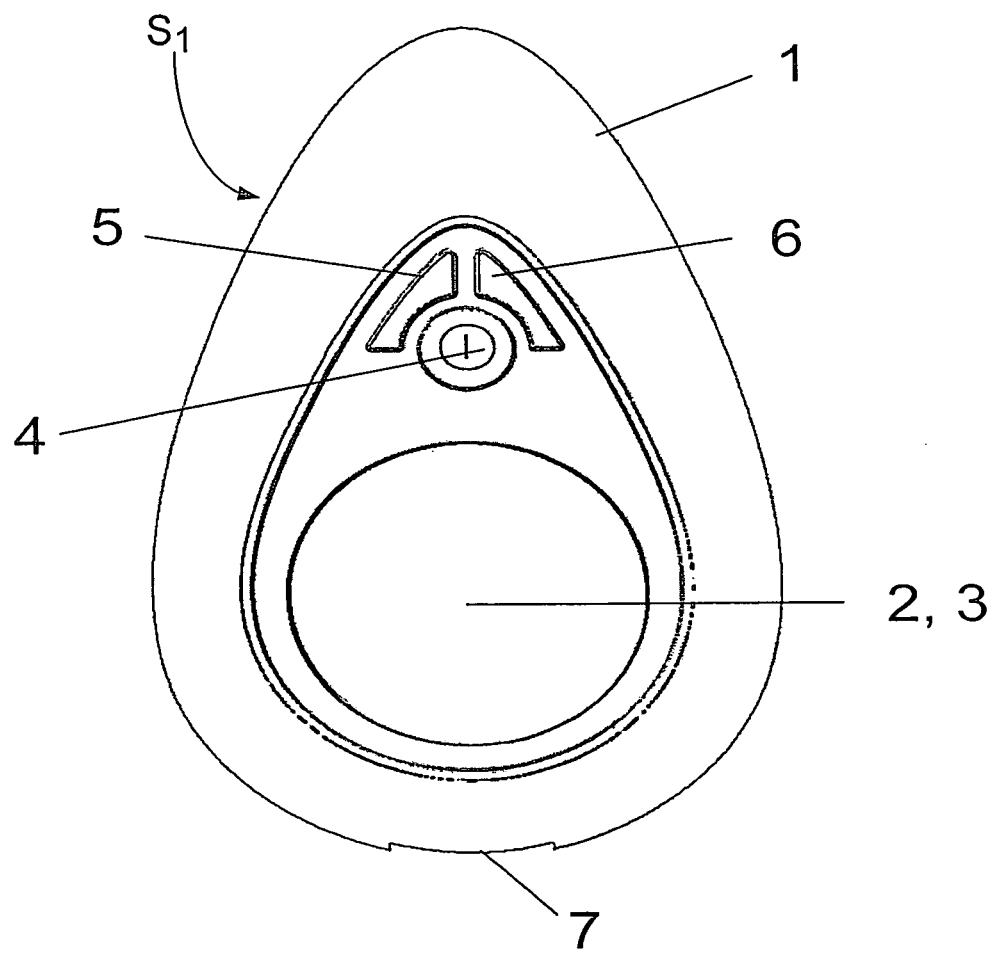
FIG. 1 is a top-down view of a sensor in accordance with an embodiment of the invention.

The invention will be more completely understood through the following detailed description, which should be read in conjunction with the attached drawings. Detailed embodiments of the invention are disclosed herein, however, it is to be understood that the disclosed embodiments are merely exemplary of the invention, which may be embodied in various forms. Therefore, specific functional details disclosed herein are not to be interpreted as limiting, but merely as a basis for the claims and as a representative basis for teaching one skilled in the art to variously employ the invention in virtually any appropriately detailed embodiment.

Numerous biometric measurements can be used in biofeedback applications, including electrodermal activity, blood oxygenation and skin temperature. These three biometric measurements can be transduced from a subject's fingertips or other points of contact with a user's skin. However, any electrical signal associated with mammalian physiology that can be measured with two electrodes can be used to provide biofeedback for use by the sensor.

Electrodermal Activity ("EDA") describes electrical properties that result from biochemical and physiological processes taking place within and on the surface of the skin. EDA can be measured using a galvanometer, one embodiment of which operates by applying a constant voltage between two sites on the skin surface and measuring the current flowing between them, in order to calculate electrical conductance. The graph of this measurement over time has two constituents: a low frequency "tonic" component (also called the electrodermal level, ("EDL")) and a higher frequency "phasic" component (also called the electrodermal response, ("EDR"). The magnitude of the tonic component differs greatly between individuals and varies slowly over time as the skin adapts to changes in the environment to achieve a homeostatic state. The phasic component is generally of more interest, as it is correlated to the psycho-physical reaction of the individual to stressful situations.

Blood oxygenation as used herein refers to the percentage of a subject's hemoglobin that is saturated with oxygen. The level of oxygenation is related to the subject's pulse rate, which in turn is correlated with their stress level. Blood oxygenation can be measured using a pulse oximeter, in which light from two light emitting diodes is passed through the tissue of the fingertip. The quantity of light absorbed at each frequency depends on the degree of oxygenation of hemoglobin within the tissue. A photodetector measures the quantity of emergent light, from which the degree of oxygenation can be inferred. Thus, the sensors described herein can measure blood oxygenation in some embodiments.

Skin temperature is also correlated with pulse rate and hence stress. Skin temperature can be measured using a thermocouple, a device whose operation is based on fact that any electrical conductor that is subjected to a thermal gradient will generate an electrical voltage, a phenomenon known as the Seebeck effect. Thus, the sensors described herein can measure skin temperature in some embodiments.

Turning now to FIG. 1, the exterior of a sensor $S_1$ in accordance with an embodiment of the invention is shown. The sensor $S_1$ has a flattened "tear drop" shaped shell 1 with two electrodes 2, 3 (not shown) situated on opposite sides of the device. An on/off switch 4 and two indicator lights 5, 6 which provide information about the status of the device (e.g. whether the device is on or off, recharging or low on power) are situated on the top surface of the shell 1. A connector 7 is located at the base of the tear drop shape. This connector allows the device to be recharged from an external power source or receive firmware and software updates. The main assembly encases all the electronic components required to (1) measure and digitize the electrodermal activity between the two fingertips and (2) communicate the resulting data stream wirelessly, in real time, to a client computing device such as a PC or mobile phone. The enclosure also houses a rechargeable battery, enhancing the portability of the device.

Figure 2:
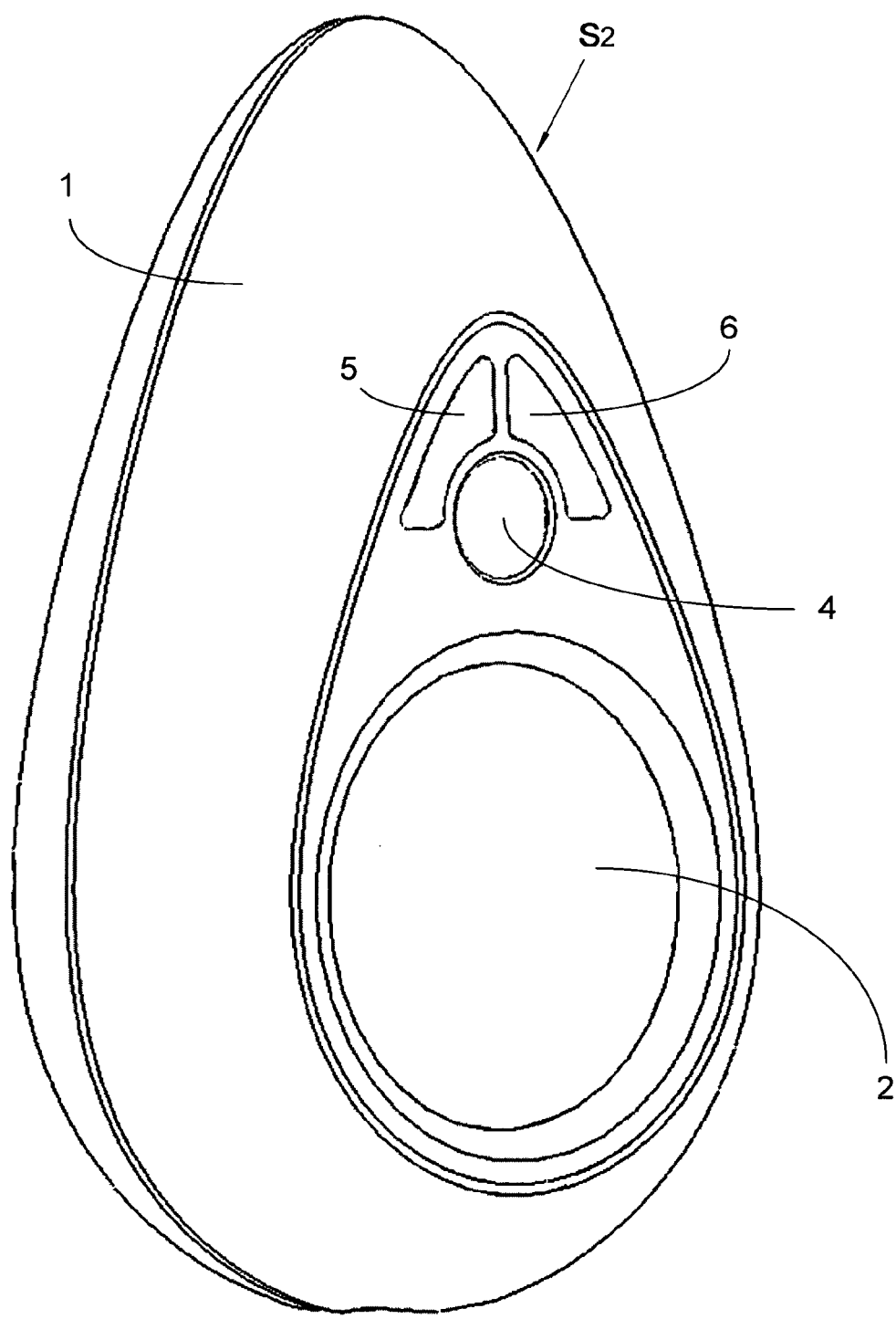
FIG. 2 is a perspective view of a sensor in accordance with an embodiment of the invention.

An alternative view of one embodiment of the sensor $S_2$ is depicted in FIG. 2. As shown, the sensor $S_2$ includes a teardrop-shaped housing with two contact surfaces 2, 3 (not shown); however other housing designs are possible. The sensor device $S_2$ is ergonomically and aesthetically adapted for comfort and ease of use. Traditional bio-feedback equipment aimed at the medical practitioner is relatively cumbersome to use. Such devices frequently employ wet electrodes (i.e. electrodes that require the application of a conductive gel or liquid in order to operate effectively). Typically, such wet electrodes are connected to a separate electronics unit via wires. In contrast, the sensor $S_2$ of certain embodiments of the invention is small, portable and wireless. This advantageous design frees the user from the limitations of wired connections, and allowing it to be used with a heterogeneous mix of computing platforms (e.g. PC/Mac, mobile phone, PDA, games console or set-top box). Further, embodiments of the invention utilize dry electrodes 2, 3, eliminating the need for advance preparation with gels or liquids. The electrodes can have any suitable 2-D or 3-D geometry. The form factor of the embodiment optimizes comfort of use when the device is held between the fingers. The enclosure shell 1 also has an aesthetically pleasing "tear-drop" shape, which is advantageous when making a consumer product that is attractive to the mass market. However, any housing that includes two separated conducting surfaces can be used with the appropriate measurement circuitry.

Figure 3B:
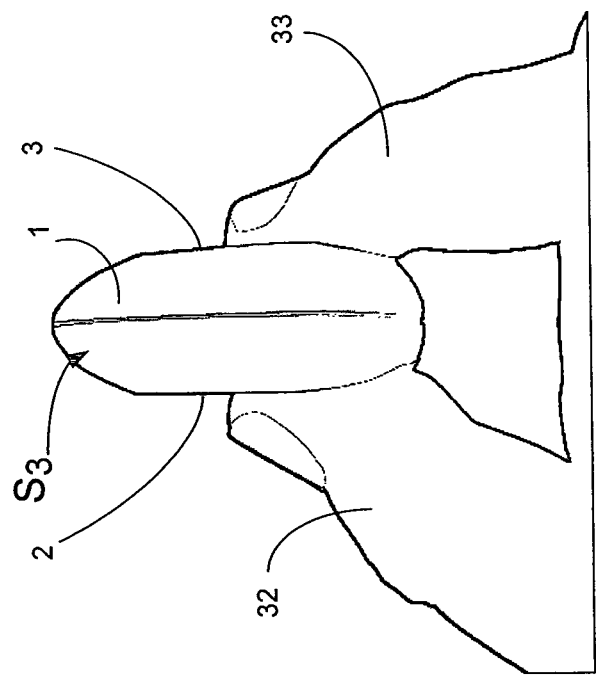
FIGS. 3A and 3B are views of a sensor in use in accordance with an embodiment of the invention.
Figure 3A:
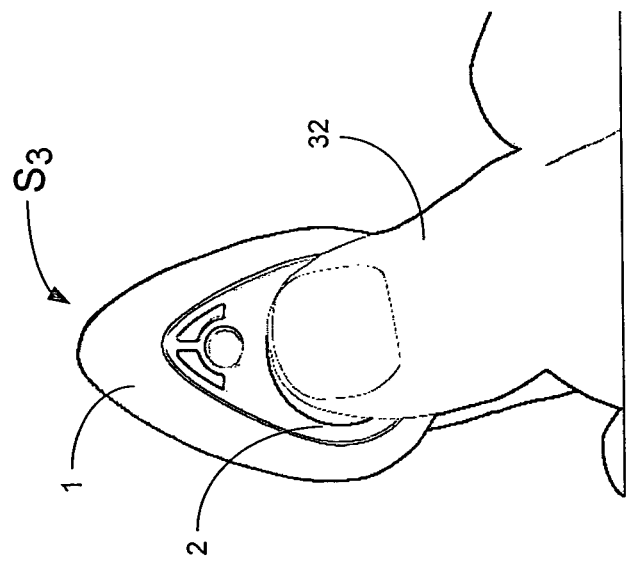

FIGS. 3A and 3B show additional views of the embodiment depicted in FIG. 1 as held by a user. As depicted, the sensor $S_3$ does not have electrodes attached to the main assembly via wires connected to the fingers, but instead provides for two electrodes on either side of the assembly, allowing the entire unit to be held comfortably between the thumb 32 and one other finger 33 of the same hand. The method of holding the device is analogous to a meditative pose where, for example, the tips of the thumb and forefinger touch, forming a loop. In FIG. 3B, both electrodes 2, 3 positions are shown.

Figure 4:
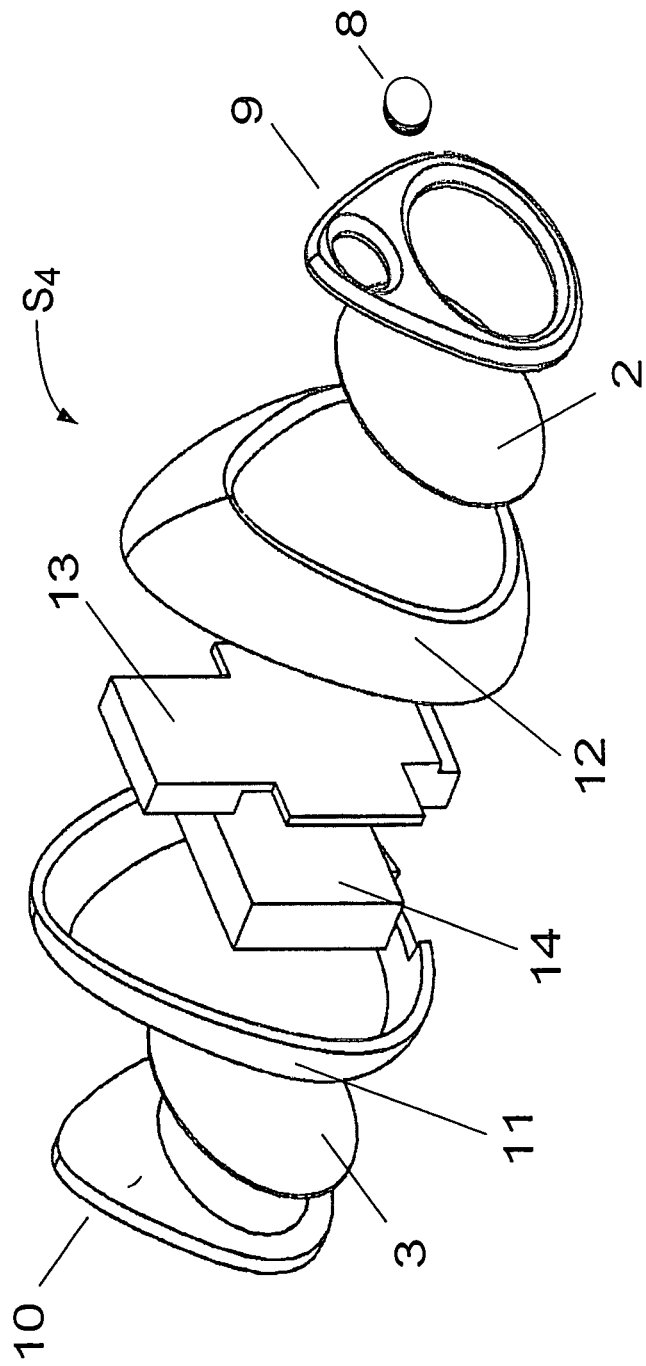
FIG. 4 is an exploded view of some of the components of a sensor in accordance with an embodiment of the invention.

FIG. 4 shows an exploded view of some of the components of the biosensor device $S_4$ in accordance with one embodiment of the invention. The device includes, two retaining rings 9, 10, two electrodes 2, 3, two main shell components 11, 12, that form the housing, a printed circuit board ("PCB") 13 and a battery 14.

According to one embodiment, the electronics contained in the PCB 13 can be sub-divided into two modules: an application-specific analog front end and an application independent digital/wireless back end. In general, the role of the analog circuitry is to transduce a biometric signal and then condition it (via amplification, filtering etc.) so that it is in a suitable form for digitization. The analog circuitry is necessarily application specific since different biometrics vary widely in their characteristics. The digital/wireless module, however, is designed to be re-usable across a wide variety of suitably conditioned analog biometric signals. In one embodiment, the module is largely application independent. For example, while the discussion below of the sensor electronics focuses on an EDA sensor, one skilled in the art should recognize that the same design paradigm could be used to measure other biometric signals without deviating from the scope of the invention. For example, a pulse rate measurement using oximetry, or a temperature measurement using a thermocouple, may be implemented, in which the analog circuitry required to sense and condition the corresponding signal is adapted for that specific application. In certain embodiments an implementation combining two or more measurements in one device is also possible.

Figure 5B:
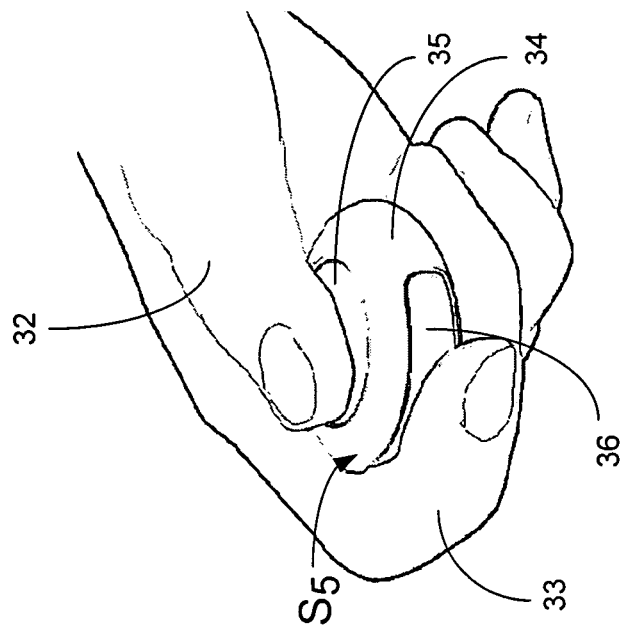
FIGS. 5A and 5B depict an alternative embodiment of a sensor in accordance with an embodiment of the invention.
Figure 5A:
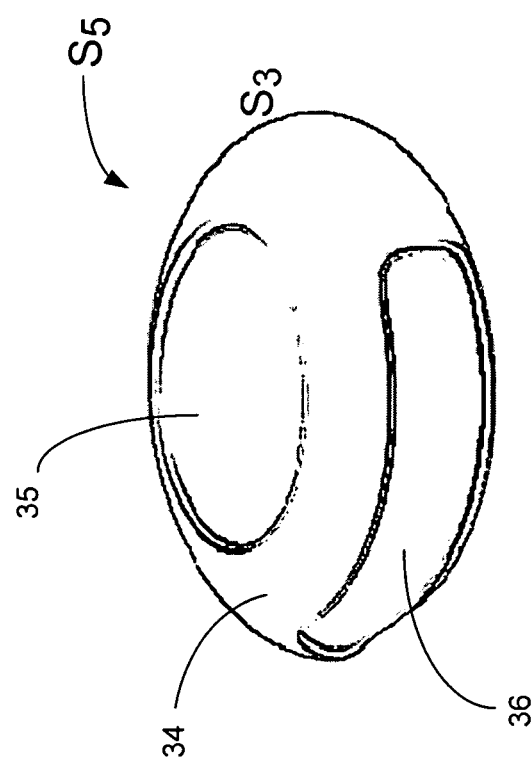

FIGS. 5A and 5B depict another embodiment of the sensor $S_5$, where the housing 34 is disc shaped. A circular disc electrode 35 is disposed near the top of the housing with a second electrode 36 wrapping around the side wall of the sensor $S_5$. In use, as shown in FIG. 5B, the user places a thumb 32 on the top electrode and wraps a second finger 33 around the side wall of the disc sensor 33. One skilled in the art should recognize that the housing shape of the embodiments described herein should not be limiting. For example the housing may take any form in which two electrodes may be held between different digits of the hand such that a meaningful bio-signal measurement may be taken. In general, any 3-D housing topology having two independently conducting surfaces can be used in various sensor embodiments.

Figure 6:
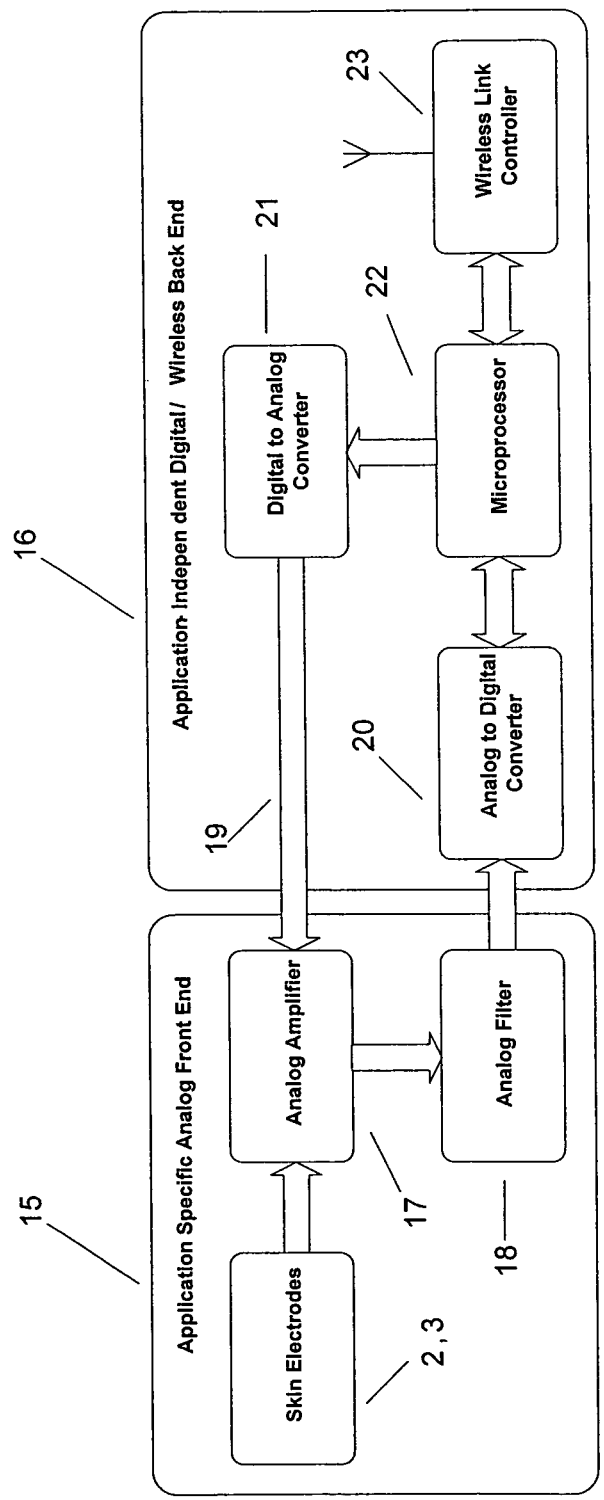
FIG. 6 is a block diagram of an exemplary architecture of a sensor in accordance with an embodiment of the invention.

A high-level architecture of the sensor electronics in accordance with an embodiment of the invention is shown in FIG. 6. The architecture includes an analog module 15 and a digital/wireless module 16. The analog module 15 includes electrodes 2, 3, an amplifier 17, and a filter 18. The sensor's electronic circuitry measures changes in skin conductivity between the two electrodes 2, 3. The circuitry may also adaptively adjust measurement parameters to track variations in a user's EDL and to control how the biometric is sampled. The circuitry further communicates, or transmits, both samples and control signals wirelessly to a client computing device for processing.

As mentioned above, the analog module 15 may be application-specific, and may be dependent on the bio-signal(s) being measured. The discussion below details embodiments where the bio-signal being measured is the electrodermal response, however, one skilled in the art should recognize that other bio-signal measurements may be implemented without deviating from the true scope and spirit of the invention.

Figure 7:
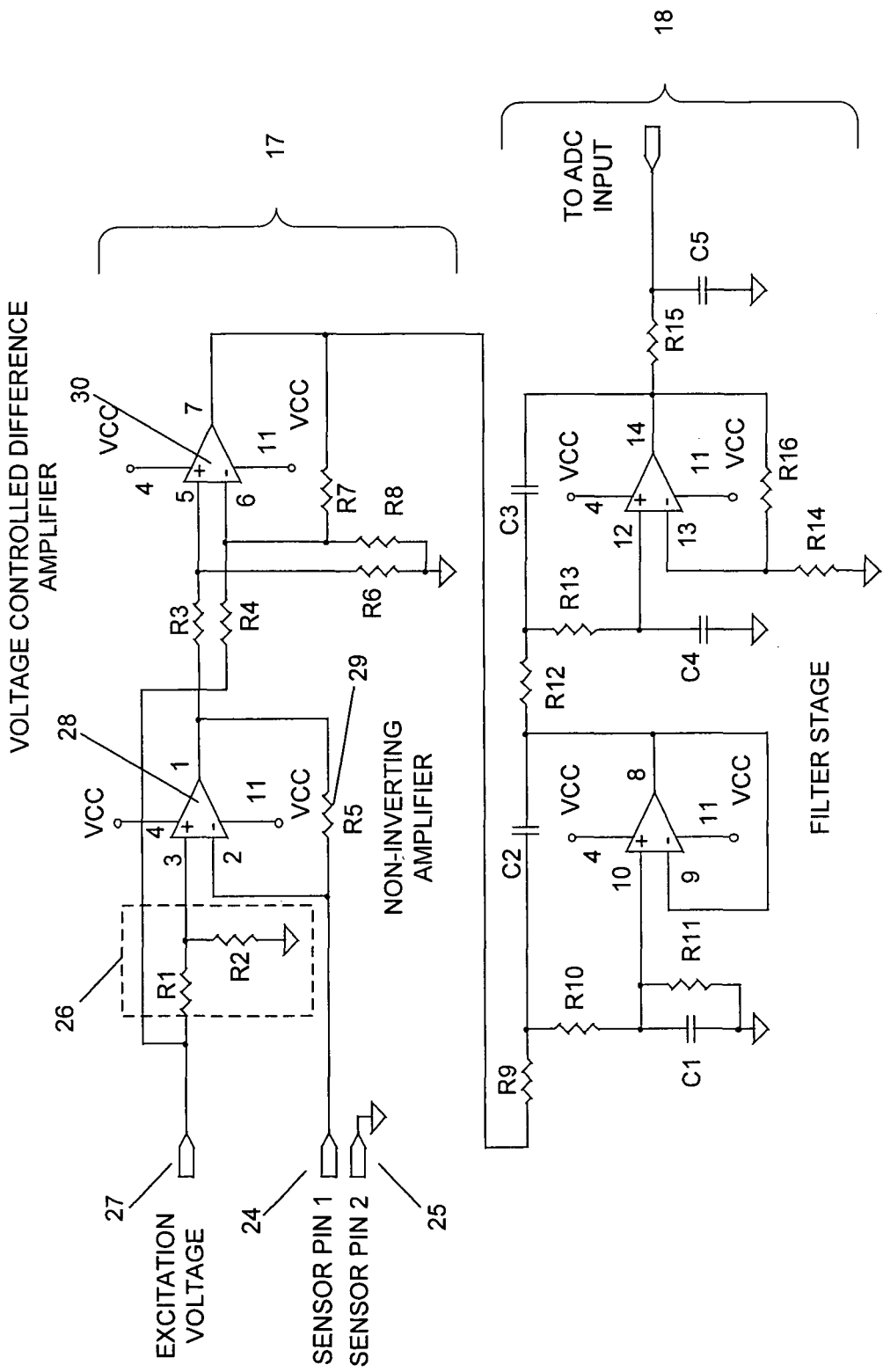
FIG. 7 is a schematic of a circuit of a sensor in accordance with an embodiment of the invention.

FIG. 7 depicts a circuit schematic of some of the analog circuitry in accordance with an embodiment of the invention. The analog circuitry resides in the PCB 13 (FIG. 4) contained within the sensor housing. Signals from the electrodes originate at sensor pin 1 24 and sensor pin 2 25. The electrodermal measurement is exosomatic (i.e. an external voltage is applied to the skin) and requires a voltage source to be applied across the electrodes in some embodiments. To a first level approximation, within certain input voltage ranges, the electrical impedance of the skin between the electrodes may be considered as a variable ohmic element. The first stage in measuring the conductance of this resistive element is to apply a constant voltage across the skin electrodes.

This constant voltage is provided via a voltage divider 26 from a constant excitation 27. The amplification stage 17 is implemented utilizing a non-inverting operational amplifier ("op-amp") 28. The amplifier gain can be set via a gain resistor 29 so that the signal is amplified as much as possible without saturating. In one embodiment, the microprocessor 22 can control the op-amp gain value by selecting from a range of resistance values. The amplified signal from the electrodes is next passed though a filter stage 18. For most electrodermal activity, the frequency band of interest, according to one embodiment, resides between approximately 0.5-5 Hz. The filter stage 18 confines the signal to the frequency range of interest, by eliminating extraneous signals such as mains (50/60 Hz) interference. One skilled in the art should recognize that other configurations of operational amplifiers, voltage dividers and other electrical components may be implemented to create a suitably conditioned signal at the input of the analog to digital converter ("ADC") 20 (FIG. 6).

As detailed above, electrodermal activity is usually described as including two components—the tonic "baseline" level and a superimposed phasic response. In practice, the phasic element normally exhibits smaller variation in magnitude compared to the tonic level. Hence, amplification of tonic and phasic components together results in a much reduced measurement resolution for the phasic constituent, which consequently could be subject to a high measurement error. Separation of the phasic variations from the tonic level prior to amplification allows for much greater accuracy of measurement of the most relevant component of the signal for biofeedback and analysis.

One embodiment of the digital/wireless module 16 (FIG. 6) achieves this separation using a microprocessor 22 to vary the excitation voltage 27 by controlling the output of a digital to analog converter ("DAC") 21. In addition to providing the excitation that is applied to the skin, the DAC 21 output voltage is applied (via a voltage divider) to the negative input of the differential op-amp 30 (FIG. 7). The output voltage from the preceding op-amp stage 28 is applied to the positive input of the differential op-amp 30, the effect of which is to subtract a proportional amount of the excitation voltage from the measured EDA, thus reducing the tonic component of the signal. The combined transfer characteristic of the two op-amps 28, 30 is that of a voltage controlled amplifier, where the controlling voltage is provided by the DAC 21. Thus, by varying the DAC 21 output voltage, the overall gain can be lowered to prevent saturation of the output in the case of a large electrodermal signal, or increased in the case of a weak electrodermal signal, in order to improve the signal to noise ratio.

The algorithm for adapting the DAC 21 voltage may be implemented in a variety of ways, such as, but not limited to, in the bio-sensor's on-board microprocessor 22, or in a signal processing routine running on a client device, the later allowing for greater flexibility. A feedback loop 19 (FIG. 6) is formed, which continuously adapts to the user's changing electrodermal activity, in order to minimize the tonic level in the signal passed to the amplifier and thus maximize the resolution of the measurement of the phasic component.

Figure 8:
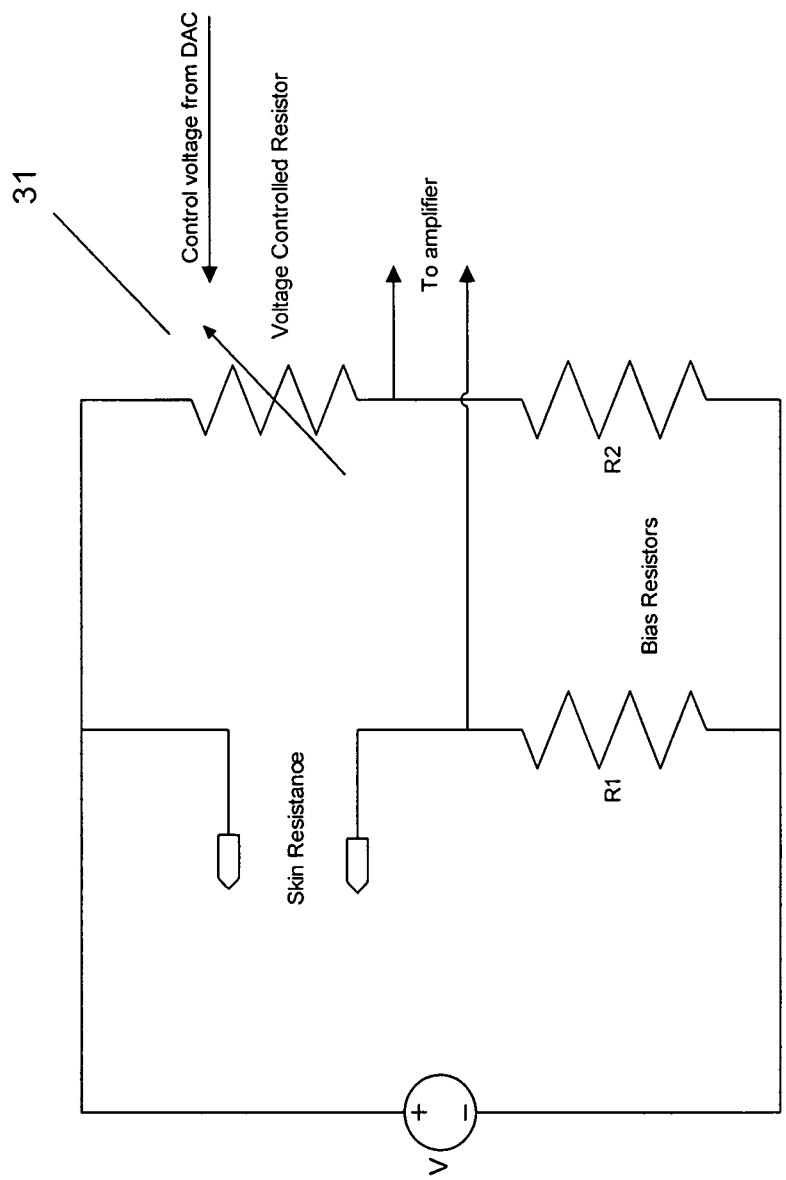
FIG. 8 is a schematic of a circuit to remove an electrodermal level from electrodermal activity, in accordance with one embodiment of the invention.

Turning now to FIG. 8, one embodiment of the invention is shown in which an adaptive Wheatstone bridge circuit 38 is implemented to separate the phasic variations from the tonic level. The circuit 38 may be continuously adapted to measure the tonic level of the user's skin conductance via software control. The general architecture of the analog design is largely the same as the embodiment depicted in FIG. 6, with the Wheatstone Bridge circuit 36 inserted between the sensor pins 24, 25 and the amplifier 17. One arm of the Wheatstone bridge is a voltage controlled resistor 31 (e.g. a junction field effect transistor (JFET) biased to operate in its ohmic region). In one embodiment, the control voltage can be supplied by a DAC whose output level is under microprocessor control. In operation, the microprocessor varies the DAC voltage (which in turn varies the voltage controlled resistance) in order to subtract as much of the tonic level as possible from the signal.

According to an embodiment of the invention, as shown in FIG. 6, the digital/wireless module 16 includes four main components: an ADC 20, a microprocessor 22, a DAC 21 and a wireless communications module 23. In one embodiment, communication between the individual integrated circuits ("IC") is via a serial bus. Different implementations of the module 16 may be utilized without deviating from the scope of the invention. For example, each component can be implemented via a dedicated integrated circuit, or two more functions can be combined on a single IC. The wireless controller 23 may be a Bluetooth module with an on-board microprocessor, or any other wireless communication standard. The use of a custom firmware application for the module allows for spare processing capacity on the module's microprocessor to obviate the need for an external processor, thus saving valuable space within the sensor housing that would otherwise be required for additional circuitry. In some embodiments, the digital/wireless module 16 also provides an on-board DAC 21, which may be used to eliminate other discrete components from the implementation. Eliminating extraneous IC's results in power saving and a reduced circuit board footprint.

In one embodiment, data communication between independent IC's is implemented via a serial bus. In an embodiment, the Inter-Integrated Circuit ("I$^2$C") standard is utilized. Such an implementation allows each IC to be individually addressed and data sent and received via a bidirectional line. The bandwidth of the serial bus is significantly higher than that required for electrodermal measurements.

The ADC 20 of the digital/wireless module 16 samples the output voltage of the analog circuitry 15 and quantizes each sample to a specific bit resolution. In one embodiment, the maximum frequency of the phasic signal is approximately 5 Hz, allowing a minimum sampling rate required to avoid aliasing of 10 samples per second. The number of bits per sample provided by the ADC 20 must be high enough to provide sufficient resolution for weak phasic signals to be measured accurately (the norm is to increase the number of bits per sample so that the quantization noise is of a similar magnitude to the noise within the analog circuitry). A bits-per-sample value of sixteen (16) is utilized in one embodiment to provide 65,536 levels of resolution, allowing for fine-grained analysis of phasic variations.

The DAC 21 converts a numeric value from the microprocessor to a corresponding analog voltage that is used to vary the excitation voltage applied across the electrodes. As previously described, in an embodiment, a second DAC may be used to set the value of a voltage controlled resistance within an adaptive Wheatstone bridge.

The wireless link controller 23 provides a "cable replacement" link between the microprocessor 22 and a client device. One embodiment of the circuitry uses Bluetooth wireless technology although the general architecture allows for this link to be provided by other wireless technologies such as, without limitation, 802.11, WLAN or Zigbee. The wireless controller 23 handles low level operations, such as baseband radio control, short term data buffering and communications protocols including error correction, while also managing higher level connection and discovery processes.

The onboard microprocessor 22 can control and configure the operation of the entire sensor, and manage the flow of data between components and also to the client device. From the sensor to the client device, the bulk of the information flow is the stream of user samples (signals). In the opposite direction (from the client to the sensor), control commands can be sent to the sensor from the client, to allow configuration of various adaptable parameters (including the amplifier gain resistance and a Wheatstone bridge variable resistance, as explained above) and to negotiate and configure various aspects of the communication link between the client and the sensor.

The on-board microprocessor 22, in one embodiment, is programmable, allowing custom firmware to be written to control the operation of the sensor. Communication between the sensor and the client is via a high-level API. In one embodiment, the API is a transaction oriented protocol for negotiating configuration and control settings and for streaming biometric data robustly over a wireless link between the sensor and client device. The bulk of the protocol is application independent; however individual applications may require extensions to the core protocol to handle specific requirements. One skilled in the art, however, should recognize the embodiments described herein are not application or protocol dependent and a variety of protocols may be implemented without deviating from the scope and spirit of the invention.

The term "client" herein refers to any device capable of connecting to and communicating with the sensor device. Examples of potential clients include, but are not limited to, desktop computers, mp3 players, mobile phones, PDA's, games consoles and set-top boxes. "Client Application" (or just "Application") herein refers to any software program running on the client that uses the biometric data transmitted by the sensor as an input. The separation of the application from the sensor itself provides a number of advantages. In such an implementation, the sensor design may be small, portable and power efficient (no need for on-board visual display unit, audio etc.). Additionally, typical client devices are designed to provide rich multimedia features, which the application may fully utilize. The sensor can be used with a heterogeneous mixture of clients, affording the user greater flexibility in choosing their preferred platform.

In certain embodiments, a majority of the software computation has been off-loaded from the sensor to the client device. This approach is advantageous as the embedded microprocessor typically provides far less processing power than that available on the client device. Additionally, in production, the firmware on the sensor typically cannot be changed, whereas application updates and improvements are relatively straightforward on client devices. Hence computationally intensive processes such as digital signal processing and analysis, graphics and audio processing and user input management are carried out by the client. In this regard, the sensor may act as a content platform (much like a games console) which can support a host of potential software applications. While the content and interaction offered to the end user will vary between applications, certain functions will be common, such as sensor control and digital signal processing. This common functionality can be implemented in the form of libraries that can be re-used between applications.

Figure 9:
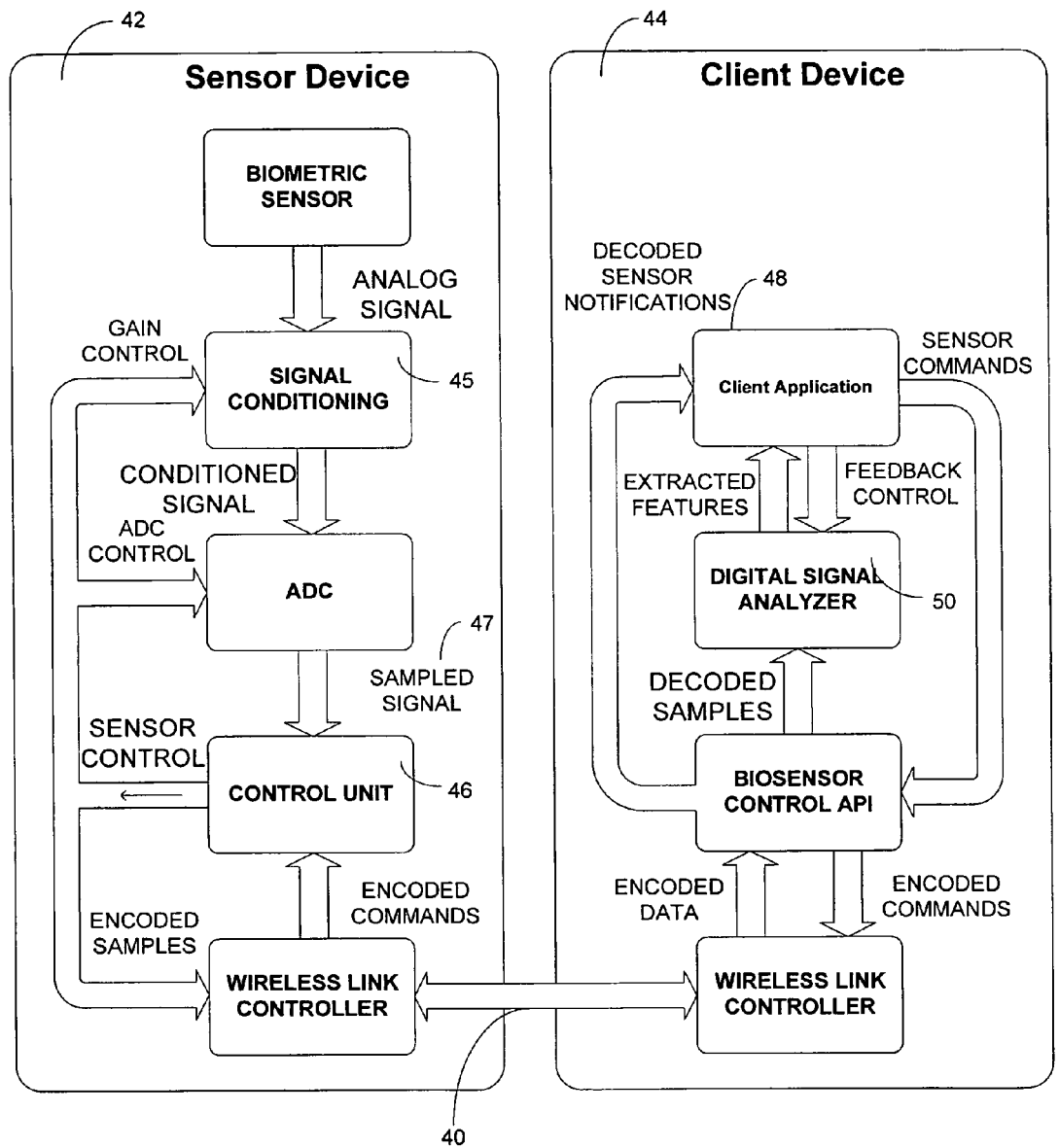
FIG. 9 is a block diagram of communication flow between a client and a sensor in accordance with an embodiment of the invention.

Turning now to FIG. 9, the general architecture of a client/sensor system in accordance with an embodiment of the invention is shown. As discussed above, the feedback loop extends over the wireless link 40 between the sensor 42 and the client computer 44 to allow the application to adapt parameters of the sensor circuitry in response to variations in the biometric data transduced by the sensor. The sensor's 42 on-board microprocessor 46 controls analog module parameters such as sampling rate, amplifier gain, and feedback (either DAC excitation, or variable Wheatstone bridge resistance) in accordance with instructions received from the application. The output of the analog stage 45 is sampled and digitized 47, and then streamed via the wireless link 40 to the client application 48. The application can use a digital signal processing ("DSP") module 50 to analyze the incoming data stream. The tasks of the DSP module 50 can include extracting useful features from the biometric data and adaptively controlling the signal conditioning parameters on-board the sensor, based on the characteristics of the received data.

With regard to electrodermal activity, the incoming data from the sensor can vary greatly due to the large differences in the electrical properties of the skin as exhibited by individual users. Adaptation of the analog circuitry by the DSP module 50 is designed so that the received data stream is always maintained within predetermined limits. This prevents the feature extraction algorithm from failing as a result of ill-conditioned input data (due to saturation or poor signal to noise ratio, for example).

One role of the DSP module 50, in one embodiment, is to perform feature extraction on the incoming biometric data stream. The DSP module 50 includes an adaptive algorithm that is capable of robustly determining the anxiety level of the user based on their biometric data. This approach is discussed in more detail below.

In traditional biofeedback systems, the extraction of usable parameters from an EDA signal has concentrated on identification of reaction pulses in the signal and rejection of motion artifact interference due to movement of the user's body during measurement. A graph of a typical reaction pulse (pulse magnitude versus time) includes of an initial, brief, steep rise followed by a slower fall-off back to a base level. The identification of such pulses is used as evidence of a psychological reaction by the user to some environmental stimulus (e.g. contextual questions posed by a tester in a therapy or polygraph session).

Figure 10:
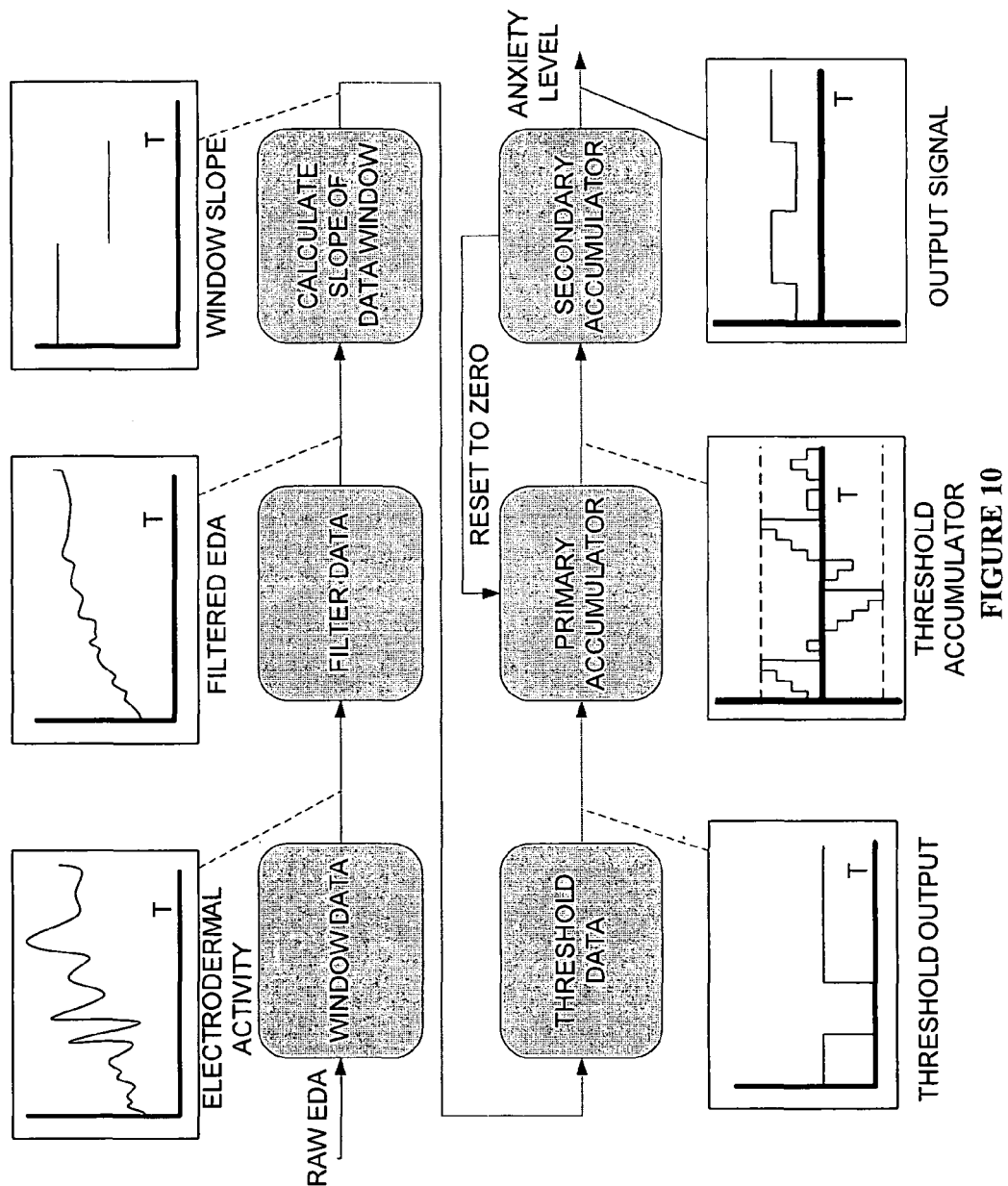
FIG. 10 is a block diagram of an adaptive signal processing algorithm in accordance with an embodiment of the invention.

Some embodiments of the invention are based on a continuous parameter adaptation with respect to the biometric signal; that is, rather than trying to identify the boundaries of a single event within the signal, the algorithm accumulates a trend counter that increments when the signal is increasing (above a threshold slope level 52) and decrements when it is decreasing (below a threshold slope value). A block diagram depicting this algorithm is shown in FIG. 10. The raw EDA data received from the electrodes over a window of time 58 is then filtered 60 and passed through a slope calculator 62. The signal is then compared to the threshold level 52 to determine if the trend counter 54 should be increased or decreased. The trend counter includes a primary accumulator 66 and a secondary accumulator 68. The application utilizes this trend counter 54 by defining an N state system that represents a user's anxiety level 70. These system states can then be mapped to some property of a virtual representation within the context of the application. An example is a character in a racing game, with three states: walking (most anxiety), running (less anxiety) and flying (least anxiety). As the trend counter increases above a pre-defined threshold 52 the system transitions to a "higher stress" state and the trend counter 54 is reset to zero 64. If the trend counter decreases below a negative threshold the system transitions to a "lower stress" state and the trend counter is again reset.

In this way, the user's anxiety levels can be continuously monitored without the need for specific event extractions. The application can weight the accumulator increment and adapt the threshold levels so that changes are optimized to user's skin type, and also to set the difficulty or timeframe for a stress management task given to the user. A test application with exercises can be used to calibrate the sensor and its output.

The output of the feature extraction system can be represented by the current state of an N-state finite state machine that represents the user's anxiety level. This state can be represented within a computer application (such as a video game) as a parameter of a virtual object. Examples may include, without limitation, the speed of a flying character, or the progress of a bird breaking out of an egg. To develop applications that allow the user to visualize their anxiety/relaxation levels in novel ways, an application toolkit may be been developed, supporting a number of client platforms.

Figure 11:
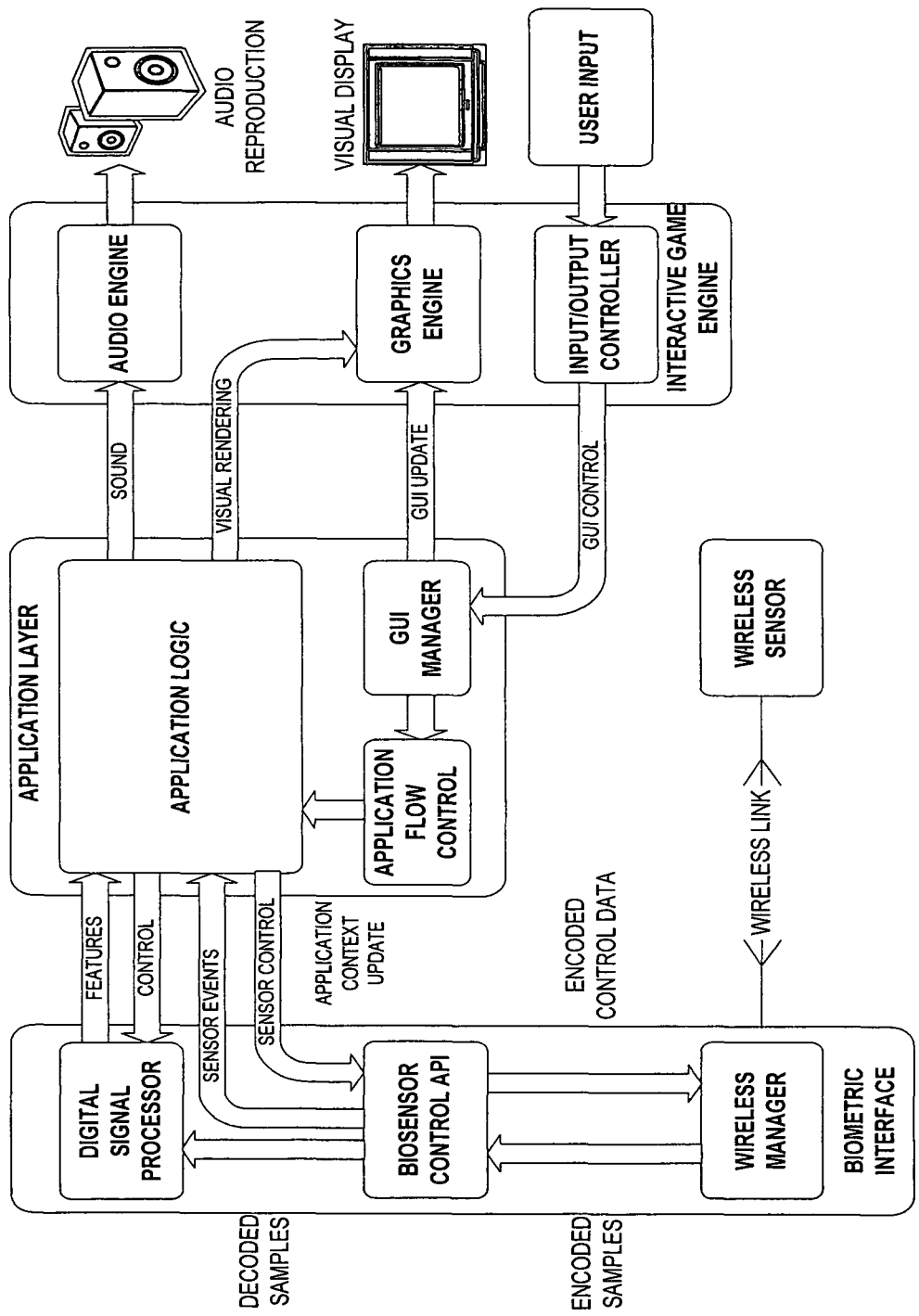
FIG. 11 is a block diagram of an application architecture in accordance with an embodiment of the invention.

FIG. 11 is a block diagram of an application using the toolkit in accordance with an embodiment of the invention. A Wireless API (e.g. Bluetooth) is a base level interface to the Bluetooth functionality of the client device, providing functionality for searching remote devices for services, connecting to devices and bidirectional streaming of data. An I/O Management System module provides a management layer for input/output data streams (for example keyboard or mouse input to the application). A Sensor Communications API encodes and decodes biometric, configuration and control data for robust transmission across the wireless link.

A Digital Signal Analysis Toolkit provides fundamental algorithms such as digital FIR filtering, least mean squares calculation of slope, windowing and thresholding, as well as an implementation of the core feature extraction algorithm that utilizes these components. A Flow Control Manager includes a finite state machine that controls the current state of the application based on user interaction. A Graphical User Interface (GUI) Manager implements common GUI elements such as menus, lists and text boxes. The graphics engine renders drawings of either 2D or 3D scenes. To be utilized in an application to create a context for presenting the user with a representation of their biometric, so that they can learn to gain conscious control over it. An Audio Engine performs reproduction of sound and music. As per the graphics engine, aspects of the audio environment can be modulated in order to provide a representation of the user's biometric.

Multi-User Embodiments

According to embodiments of the invention, the methods, systems, and devices described herein can be used cooperatively. That is, multiple users can participate in an activity such that biometric data is used cooperatively within a group of users.

Embodiments of the invention involve a group of two or more people carrying out a shared task in a virtual environment, where the task can only be completed by the members of the group co-operatively relaxing. In certain embodiments, the group's progress can be represented by the state of an animation or audio piece. The progress of the task is shown simultaneously to all members of the group, giving each member feedback on the overall relaxation level of the group.

An embodiment of the invention includes multiple biometric sensor devices (at least one per user) that monitor a biological signal such as EDA, blood oxygenation, brain electrical activity, muscular electrical activity, heart rate or temperature. A data stream from each biosensor is transmitted to at least one client device (such as a PC, mobile device, PDA, or set top box). In certain embodiments, a signal processing module on the client device analyses each incoming data stream to extract psychological arousal (stress/relaxation) information on a per-stream basis. In another embodiment, the signal processing module combines data from separate members of the group into one variable that represents the group's combined stress level. In yet another embodiment, a graphical rendering system (2D or 3D) displays an animation which transitions over time, depending on the combined stress/relaxation level of the group. Additionally, (an audio system may play sounds and/or music, whose characteristics are modulated based on the combined stress/relaxation level of the group.

Further embodiments of the invention are based on the fact that certain biometric signals exhibit known correlates with psycho-physiological states, such as high levels of arousal of the sympathetic nervous system, which in turn is related to the everyday concept of an individual's stress and relaxation levels. One such embodiment utilizes heart rate variability ("HRV"), a biometric based on the variability of the time period between successive beats of a person's heart. In general, this variability increases as a person becomes stressed and reduces as they relax. HRV can be extracted by analysis of a number of biometric measurements related to heart rate, including EKG and pulse oximetry. Such measurements can be made via a biosensor connected to the user, and sent to a computing device for analysis and extraction of the HRV. In another embodiment, the biometric used to extract a user's stress level is the electrodermal activity resulting from variations in skin conductance. An increase in conductivity is strongly correlated with sympathetic arousal and therefore indicative of an increase in stress level. One skilled in the art should recognize that many biometric correlates of psychological stress level can be measured or monitored and embodiments of the current invention are not limited to those correlates defined above.

In one embodiment, a stress measure is extracted from each member of a group of users and the individual measurements are combined to create an aggregate metric of the group's overall relaxation level. The aggregation can be done in many ways, including, but not limited to, selecting the group metric to be the stress level of the most or least stressed member, the mean or median stress level of the group or some function of the group members' individual levels over time.

According to one embodiment, the group metric can be used as a modulating parameter in an audio/visual presentation to the group. This may include an animation system which renders a scene that changes as the group relaxes. An example of this may include the rendering of a scene that changes from a storm to sunshine as the group relaxes. In another embodiment, the group metric may also modulate the playback of a musical piece consisting of multiple layers. Initially, only a single layer of the piece is played. As the group relaxes, further layers are revealed.

Embodiments of the invention provide both a context for cooperative bonding within the group, as well as an exercise to reduce the overall stress level of the group, in order to motivate group members to become more relaxed.

In one embodiment the application is defined as a massively-multiplayer online game ("MMOG"). The MMOG consists of a distributed network application, in which multiple users participate in a persistent virtual world via a client application running on a personal computer or mobile device. The client device renders a scene, with each user being represented by an avatar that is flee to move within the virtual world. Conventionally, users interface with the world via input devices such as keyboards, mice, tracker balls, joysticks and game pads. In the current embodiment, each user also interfaces with the MMOG client via a biosensor that transduces electrodermal and/or blood oxygenation data directly from the user. As described above, the user's stress level can be extracted from the transduced signal, and used to modulate the update of the virtual world to create a group biofeedback loop.

Figure 12:
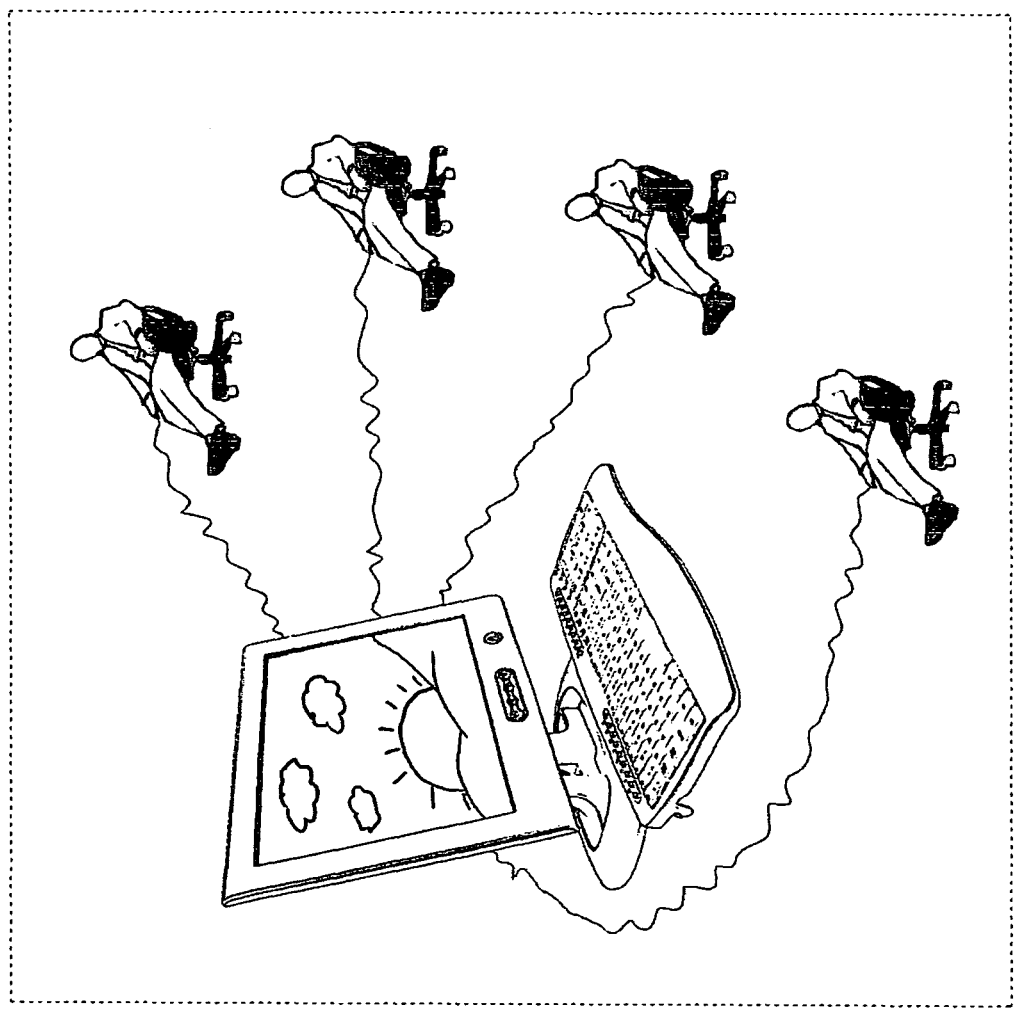
FIG. 12 is a block diagram of a cooperative relaxation application in accordance with an embodiment of the invention.
Figure 13:
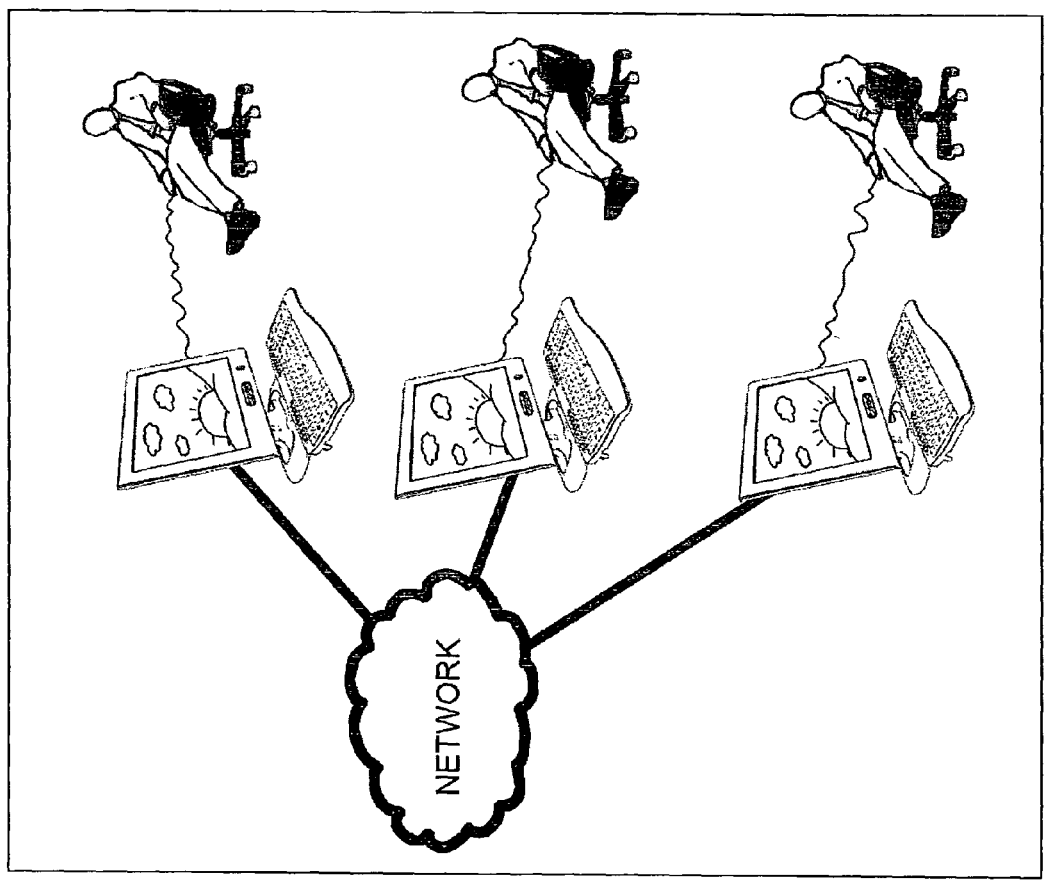
FIG. 13 is a block diagram of a cooperative relaxation network structure in accordance with an embodiment of the invention.

In another embodiment, as shown in FIG. 12, the MMOG includes a virtual environment in which several users can meet at a specific location within the environment and, while all connected via biosensors to their client computing devices, participate in a group biofeedback process where each user contributes, via their relaxation level, to a parameter that modulates properties of the virtual world. In this embodiment, the property being modulated can be context dependent and be incorporated into the framework of the application as a group task. One example is using the group relaxation level to modulate the weather within the virtual world. The group is given feedback on its combined relaxation level by viewing changes in the weather, from dry heat to rain clouds. The changes elicited by such group action can be further linked into the framework of the virtual environment by being mapped to a task to be performed by the group in order to reach some context defined goal, for example to create rain so that virtual crops may grow.

According to one embodiment, the client device may be either a personal computer with visual and audio outputs (such as a computer monitor and speakers), or a mobile computing device with audiovisual capabilities such as a mobile phone. The client device may also contain a wireless communication unit, such as a Bluetooth transceiver, by means of which it can wirelessly connect to, and acquire data, from other Bluetooth-capable devices. In one embodiment, the subsystem that analyses and utilizes the biometric signals is called an "E-motion Engine", and includes both client- and server-side components.

In another embodiment, the biosensor includes a galvanometer for reading changes in skin conductance (EDA) and a pulse oximeter for detecting changes in blood oxygenation. These analog signals are acquired and converted to digital signals within the housing of the biosensor.

The EDA, according to one embodiment, is acquired at sixteen (16) bits per sample and at a sample rate of thirty-two (32) samples per second. The blood oxygenation data is acquired at sixteen (16) bits per sample and at a sample rate of one hundred twenty-eight (128) samples pre second. The digital data is then sent wirelessly via Bluetooth (or other wireless protocol) link to the client device, for processing.

Figure 14:
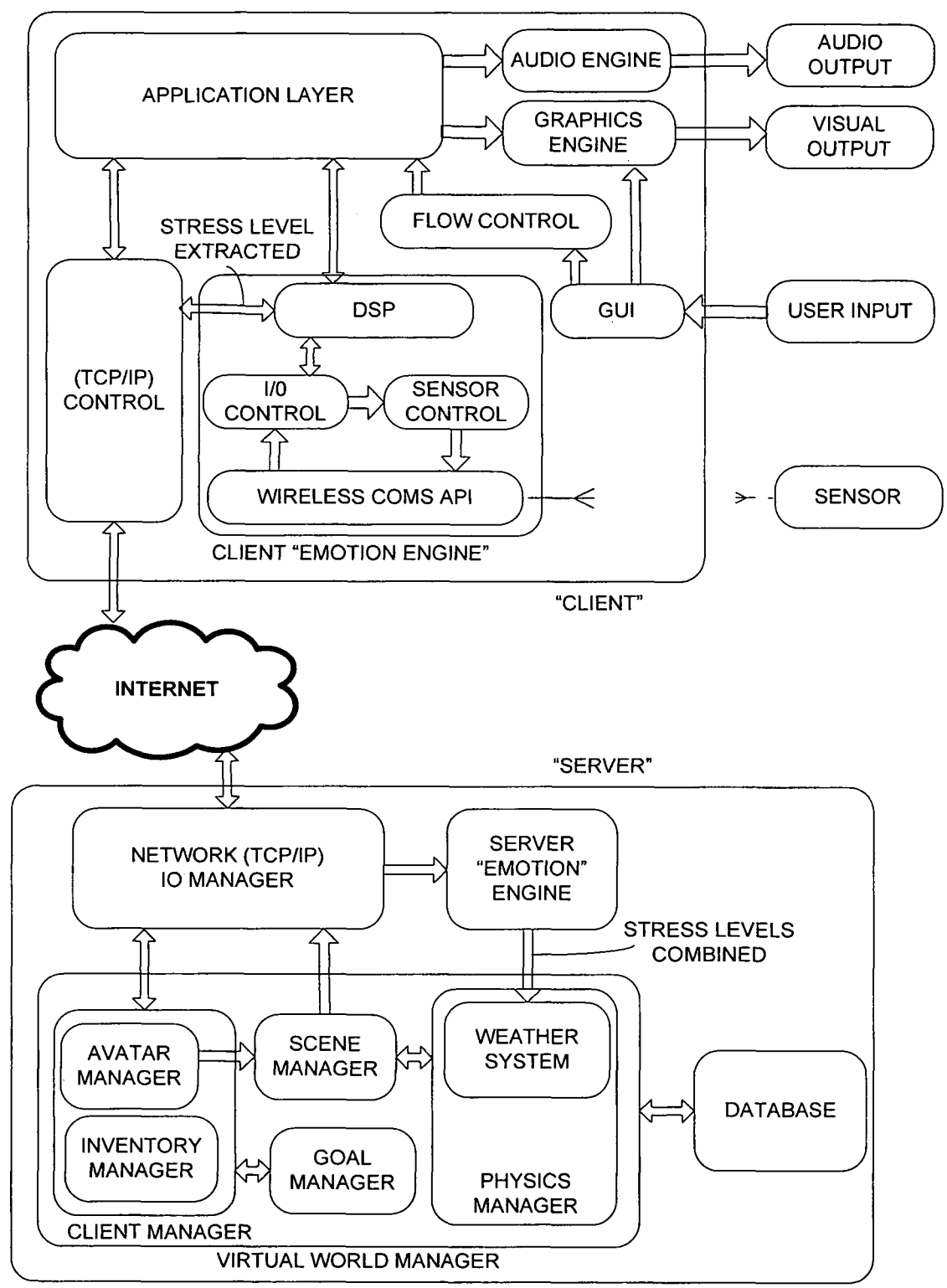
FIG. 14 is a block diagram of a client server architecture of an entertainment application with cooperative relaxation in accordance with an embodiment of the invention.

One embodiment of the client application, as shown in FIG. 14, contains a wireless link, such as a Bluetooth IO system, that manages the bi-directional flow of data between the biosensor and the client application. The client application also implements an Internet (TCP/IP) IO system in order to manage the bidirectional flow of data between the client and the server application. The Emotion Engine receives the input from the biosensor via the Bluetooth IO system. The engine includes a communication API and an IO manager and decoder module that parses and interprets the input data stream from the biosensor, using a custom data protocol. The Emotion Engine client (digital signal analysis toolkit) provides basic signal processing algorithms, such as digital FIR filtering, least mean squares calculation of slope, windowing and thresholding. It also provides an implementation of the core feature extraction algorithm that utilizes these components. The digital signal processing component of the application takes as its input two biometric data streams: the electrodermal and blood oxygenation signals. The engine also includes a hardware controller for processing and transmitting control signals to the biosensor. A flow control manager implements a finite state machine to control the user's interaction with the client application. The graphical user interface ("GUI") system implements common GUI components such as menus, lists and text boxes. A graphics engine and scene manager perform 3D rendering. An audio engine allows for playback of music and sounds. In combination, the graphics and audio systems create a context in which the user receives compelling feedback, and a strong motivation to exercise conscious control over their biometrics.

According to one embodiment, the EDA is first low pass filtered (cutoff frequency 5 Hz), and the stream is then processed as a sliding window of sixteen (16) samples (0.5 seconds of data, at a sampling rate of 32 Hz). A slope calculation is made on the window of data using a least squares algorithm. This resulting slope value is then compared to a series of threshold levels which are modulated by the user's EDL (tonic level). In general, positive slopes correlate to higher stress and negative slopes correlate to lower stress. Based on this comparison, the stress level of the user is mapped to a single parameter. The EDA data stream represents a fast response (low latency) measure of changes in the user's emotional state.

The blood oxygenation data stream is first low pass filtered (cut-off frequency 40 Hz) and, on each heart beat, a peak-to-peak measurement of the current beat period is made. This period is added to a sliding window of sixteen (16) beat period samples (implemented as a circular buffer) and a calculation is made of the standard deviation of the beat periods at each heart beat. Increases in this value are correlated with increased user stress while decreases in this value are correlated with less user stress. The heart rate variability (HRV) measurement results in higher latency, but provides a more accurate indication of the user's emotional state (as determined from their stress level) over longer timescales.

The MMOG server application acts as a hub for the group of client applications connected to it. FIG. 14 shows the key components of the MMOG system. The server application contains several component parts including an Internet IO management system which provides a management layer for TCP/IP input/output data streams. The server application also includes an Emotion Engine server, which retrieves data from client Emotion Engine systems, and combines this data to create a single parameter that is indicative of the group of users' emotional state. This parameter is then used to modulate the update of an object or objects maintained by the World Scene Controller system. The World Scene Controller is responsible for the update of all objects within the virtual world, including the users' avatars. A Database Manager allows for persistent storage of all object data within the virtual world, including all avatar data. A Physics Manager provides a physical simulation that controls the movement and physical interaction of objects and avatars in the virtual world. A Weather System (a subsection of the Physics System) updates the weather within the virtual world, managing changes ranging from wind levels to thunder storms in different areas of the map of the virtual world. The client application is responsible for maintaining, over time, the synchronization of the local world state with the server's representation of the world state.

The server component of the Emotion Engine receives biometric data from the client's biometric subsystem. This data is sent from the client together with normal control data regarding the client avatar's movements and actions. Each client's measure of the user's stress level is sent to the server application, where the individual measurements are combined into a single metric that is representative of the overall stress/relaxation level of the group of users. In one embodiment, the combined metric is the maximum value of the set. Let $L_i$ denote the stress level measured by client i, where i ranges from 1 to N. Then, the group stress level, Lg, is defined as $$L_g = \mathrm{Max}(L_1, L_2, \ldots L_i, \ldots, L_N)$$

This group stress level, Lg, is then used as an input parameter to a further system running on the server that controls some aspect of the virtual world. One example is as an input to the Weather Control System, where Lg is used to vary the virtual climatic conditions in that region of the virtual world where the group of client avatars are located. This weather state is then fed back to each client's audiovisual rendering system where the user can see and hear the combined effect of the group on the weather system. Consequently, the aggregate relaxation level forms part of a group biofeedback loop. The biofeedback process in this instance is further defined in terms of a task within the virtual world, in which the group must relax together long enough to produce rain in the virtual world, that in turn allows virtual crops to grow.

In another embodiment, a group of users participate in a standalone application, each user interacting with the application via a biosensor. Each biosensor transduces electrodermal activity and blood oxygenation from the user's body. In one embodiment, a measure of the group's relaxation level is calculated and used as a controlling parameter for an animation and audio rendition of an orchestra playing a concert. The musical piece being played by the orchestra is comprised of multiple layers. As the group relaxes together, extra layers of the music are added and become louder until, after a certain amount of time, the full depth of the piece is audible. An additional feature of this application maps individual subgroups of the total user group to different sections of the orchestra (such as strings or wind) so that relative relaxation levels of the subgroups can be gauged.

One context of such a standalone application is a classroom setting, where students relax together, in an entertaining way, before the start of class. As a further refinement of this context, the class could consist of a group of students who suffer from hyperactivity or anxiety problems. Another possible context is a corporate setting, where work colleagues relax together as a way to increase productivity and promote team building. Yet another possible context is clinical group therapy, in the field of anxiety or anger management.

Virtual Agent Embodiments

Embodiments of the invention also include a virtual agent simulation that includes biofeedback via a biosensor among its modes of user interaction. This biofeedback interaction is related to an internal drive of the virtual agent and modifies the behavior and state of the virtual agent over time. In one embodiment, the biofeedback interaction is related to the "feeding" of the virtual agent. The virtual agent's current state of wellbeing requires the user to spend time "feeding" the agent at regular intervals. This "feeding" process involves the user connecting to the application via a biometric sensor. The biometric sensor data is processed to extract information that is correlated to the user's stress/relaxation level. The rate of feeding of the virtual agent is proportional to the level of relaxation reached by the user during the feeding session.

Figure 17:
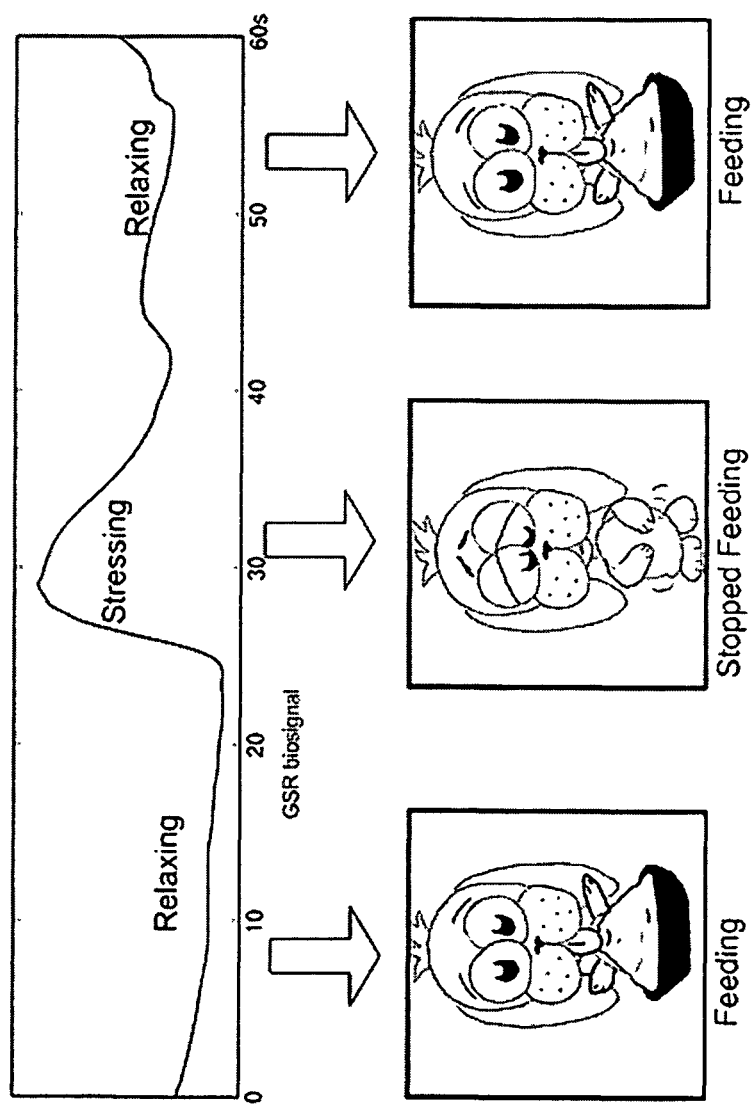
FIG. 17 is a block diagram showing mapping from signal data to character behavior in accordance with an embodiment of the invention.

The mapping of feeding of the virtual agent to the relaxation level of the user allows for a conceptual mirroring between the wellness of the virtual agent and the wellness of the user. A signal processing component of the application calculates the stress/relaxation level of the user. If the stress level is below a threshold value the user is deemed to be relaxing and this relaxation is used to feed the virtual character. During this virtual feeding process a representation of the user's stress/relaxation is shown to the user, as is an animation showing the virtual agent feeding. The feeding is, in itself, a biofeedback session where the user is given continuous feedback of his/her stress/relaxation state and also has the goal of relaxing for a required amount of time to sate the virtual agent's hunger. This visual feedback is depicted in FIG. 17 as an indicator bar showing the progress of the feeding session.

A virtual agent that survives on a user's relaxation levels, according to one embodiment, provides a user-friendly context in which a person can find time to relax regularly and keep track of their overall relaxation routine in a simple way (via the state of the agent).

Figure 15A:
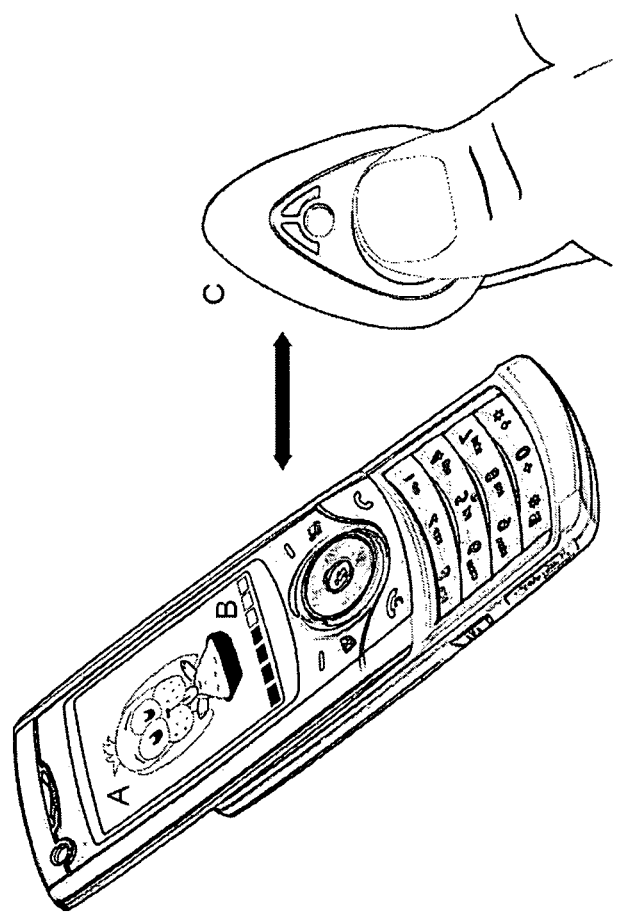
FIG. 15A is a block diagram showing a portable GSR biosensor and mobile device virtual pet in accordance with an embodiment of the invention.

FIG. 15A shows a virtual character application running on a mobile client. The client device provides the execution environment to simulate the agent's internal states as well as provide a graphical user interface to the user to manage the flow of the application and display of the character's behavior on screen.

In one embodiment the application runs on a mobile computing device (a mobile phone with a program execution environment and display screen). According to one embodiment, the mobile device has the capability to wirelessly connect to a biosensor and analyze biometric data streamed from the sensor to the mobile device. In this embodiment, the biosensor contains a galvanometer combined with an oximeter, for transducing the user's electrodermal activity and blood oxygenation levels. These biosignals are sent to the mobile device, where they are processed by the application to extract known correlates with the user's stress and relaxation levels.

The client application contains several component parts including a Bluetooth IO System that provides management of data sent to, and received from the biosensor. A Communication Protocol System parses the input stream from the sensor and interprets the data according to a custom protocol. The Emotion Engine Client (digital signal analysis toolkit) provides basic signal processing algorithms such as digital FIR filtering, least mean squares calculation of slope, windowing and thresholding. It also provides an implementation of the core feature extraction algorithm that utilizes these components. A virtual agent state management system maintains a representation of the state of the virtual character, defining the total set of possible states and drives that, over time, cause the behavior of the agent to change. A flow control manager provides a finite state machine that controls the user's interaction with the client application. The GUI system implements common user interface components such as menus, lists and text boxes. A Graphics Engine manages the visualization of the virtual character. An Audio Engine provides sound and music playback within the application.

According to one embodiment, the digital signal processing component of the application takes two biometric data streams as its input: electrodermal activity and blood oxygenation. The electrodermal activity data is first low pass filtered (cutoff frequency 5 Hz), then processed as a sliding window of sixteen (16) samples. A slope calculation is made on the window of data using a least squares algorithm. The resulting slope value is then compared to a series of threshold levels which are modulated by the user's EDL (the tonic level). In general positive slopes correlate to higher stress and negative slopes correlate to lower stress. Based on this comparison, a single value parameter is mapped to the user's stress level. The EDA data stream represents a fast response (low latency) measure of changes in the user's emotional state.

The blood oxygenation data stream is first low pass filtered (cut-off frequency 40 Hz) and, on each heart beat, a peak-to-peak measurement of the current beat period is made. This period is added to a sliding window of sixteen (16) beat period samples (implemented as a circular buffer) and a calculation is made of the standard deviation of the beat periods at each heart beat. Increases in this value are correlated with increased user stress while decreases in this value are correlated with less user stress. The heart rate variability (HRV) measurement results in higher latency, but provides a more accurate indication of the user's emotional state (as determined from their stress level) over longer timescales In one embodiment, these metrics are used as inputs to a simulation of a virtual agent. The simulation internally represents a series of states, each analogous to a state of being of a real animal, such as "sleeping", "eating", "playing" or "hunting". A series of drives model how the agent moves between different states over time, i.e. the hunger drive may move the agent from being "playful" to start "hunting" for food. The relaxation metrics extracted from the user are used as inputs to this system to "feed" the agent and so sate the hunger drive over time.

In one particular embodiment the virtual character is a pet puppy. At the first running of the application, the user is given a selection of puppies to choose from. Once the user has made their choice, their puppy appears on screen, waiting to interact with the user. The puppy's behavior can be portrayed as playful and desirous of interaction with the user. The user can interact with the puppy via a series of on-screen icons, such as bringing the dog for a walk or playing "fetch". The internal state of the puppy represents an autonomous system which modulates its behavior based on these interactions.

The application will measure the elapsed time during and between sessions and calculate changes in the internal drives and states of the puppy. The drive for hunger grows over time and can be represented visually (for example, by the puppy walking over to the feeding bowl). This behavior will increase in regularity over time until a user connects to the application via a biosensor. The application analyses the user's biosignal and extracts information about their stress/relaxation level. The amount the puppy is fed is related to length of time of the biofeedback session and also the levels of relaxation achieved during the session.

Figure 15B:
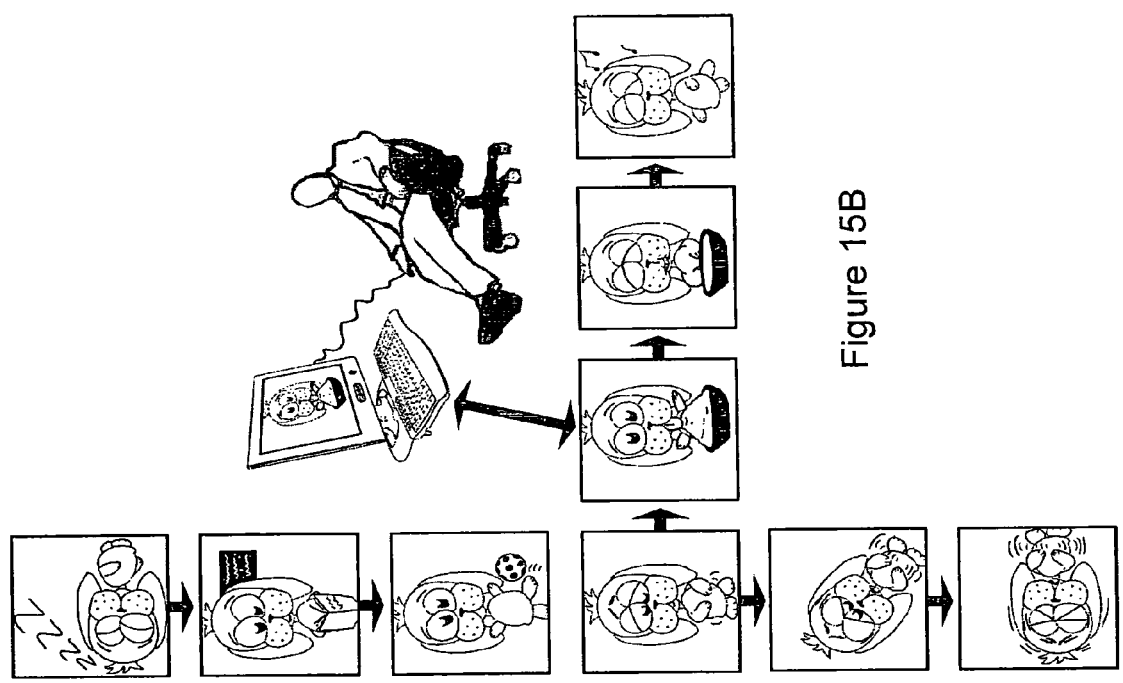
FIG. 15B is a block diagram showing a flow of the internal states of a simplified virtual creature in accordance with an embodiment of the invention.
Figure 16:
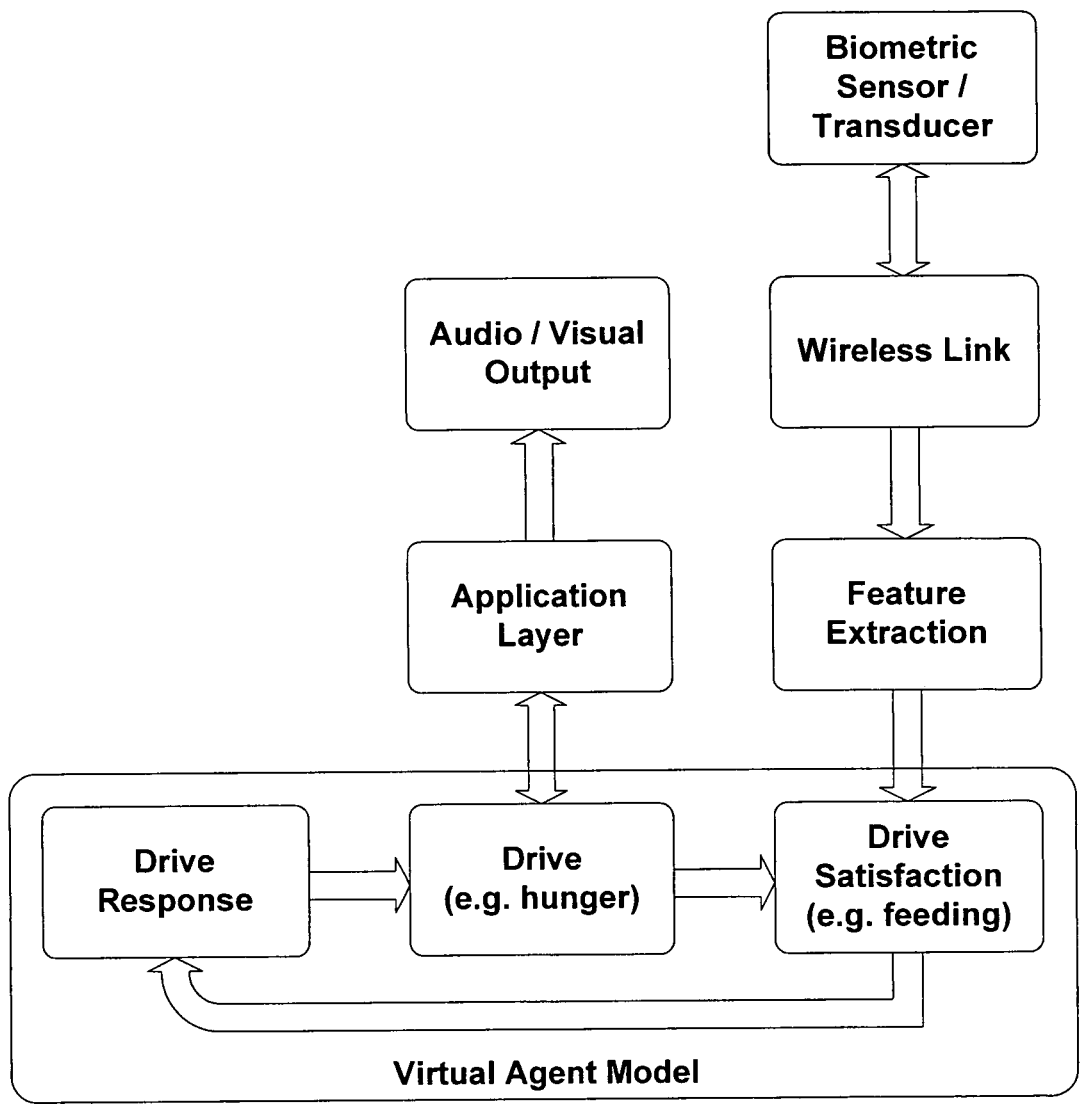
FIG. 16 is a block diagram of a virtual agent model architecture in accordance with an embodiment of the invention.

FIG. 17 shows an outline of the feeding process and a general mapping between the user's electrodermal signal and the visual representation of the virtual pet. If the user does not feed the puppy regularly, it will exhibit lethargic behavior, eventually leading to it becoming sick and unresponsive. This change in states is shown in FIG. 15B. Over several sessions, the puppy is seen to grow into mature, adult dog. The feeding sessions, in themselves, are biofeedback processes and so the user is given visual feedback about his/her relaxation levels in real time. These sessions can be represented to the user as mini-games in which different goals may have to be achieved in a given timeframe, so that their virtual pet can be fed (for example winning a "relaxation race" to garner food). These sessions can be also simply described by showing the virtual puppy eating, in addition to an indicator showing the progress made in the current feeding session. (Indicator shown as B in FIG. 15A). The wellness of the virtual dog reflects the user's attention to the dog over time and especially the regularity of feeding sessions via the biosensor.

One embodiment includes the ability to transfer the state of the virtual agent between client devices. The application running on a mobile client device (in this case, a mobile phone with a display element) is synchronized with a PC, and data describing the full internal state of the agent is transferred between the two devices. In this way the representation of the virtual creature can be seen as having a continuous existence across multiple devices.

In another embodiment, the virtual pet can be allowed to "socialize" in a virtual environment. The pet's state is uploaded, over a network, into a virtual environment where two or more pets can interact autonomously. This environment can be viewed by a user so that he/she can see how their virtual pet interacts with other virtual pets.

The same concepts can be applied to a wide range of virtual agent embodiments, including but not limited to, an artificial plant or garden where the users relaxation levels are mapped to rain/water to keep the plant life alive, a virtual goldfish in which the artificial fish or group of fish that are fed via relaxation/stress levels, a general artificial agent where embodiments are designable and modifiable by the user.

Mobile Polygraph Embodiments

In another embodiment, an application runs on a client device connected to a biosensor and acts as a simple polygraph. The polygraph traces one or more on-screen graphs each of which represents a biometric data stream having known correlations with user stress levels.

In one embodiment the biosensor transduces electrodermal activity on the surface of the skin. The graph displayed on screen represents a sinusoidal function which has its amplitude modulated by the current rate of change of the skin conductivity signal. A large increase in conductivity maps to a large amplitude sinusoid trace while a fall in electrodermal conductivity maps to a zero amplitude sinusoidal trace, i.e. a flat line. This mapping produces a graph on screen that is a similar to the early mechanical polygraph traces with which many people are familiar. In this way, the user can clearly associate high sinusoidal amplitude with high stress. This embodiment can be used as a simple "lie detector" where one person asks another person questions while viewing the polygraph trace on screen.

Example Protocol

Various wire-based protocols, such as USB, Ethernet, and FireWire, and wireless protocols, such as Bluetooth and Wi-Fi, can be used to facilitate communications between the biometric sensor and a master device (e.g. mobile phone, PDA, iPod or desktop computer). In addition, various proprietary protocols can be developed for communicating between the biometric sensor and another device.

In one embodiment, the biometric sensor's protocol is transaction oriented. Two types of transaction exist—requests and notifications. A request transaction from the sender can be acknowledged by the receiver, i.e. the receiver sends a response to the sender to (a) indicate the status of the request (success or failure), and (b) return the appropriate information (if any) sought in the request. A notification transaction is unidirectional: the sender expects no response, and the receiver should not send one. In another protocol embodiment, all transactions issued by the master device to the biometric device are of the request type, while all transactions issued by the biometric device are of the notification type. This is to minimize the transaction processing overhead on the biometric device, by obviating the need to parse responses from the master device.

Each complete transaction is comprised of one or two messages for a one protocol embodiment. A notification includes a single message; a request consists of two messages—the request and the response. Each notification or request message can be demarcated by begin and end symbols. For example, the begin symbol can be immediately followed by a TRANSACTION ID, which identifies the particular transaction type that this message refers to. A payload can be used in the protocol that contains additional information relevant to the transaction type. A response message has an additional field to indicate the status of the corresponding request—success or failure.

In one embodiment, the format of the response message is dictated by the corresponding request, in that the transaction ID of the response must match that of the request, and the status field must indicate whether the request resulted in success or failure. The transaction protocol is byte-oriented, i.e. the atomic unit of information in each transaction is a byte, in some embodiments.

The table below summarizes all valid transactions for one specific biometric apparatus protocol embodiment.

| Transaction ID | Type | Description |
| --- | --- | --- |
| VERSION | Request | Requests that the Sensor device send the version of the firmware that it is running |
| PIN | Request | Requests that the Sensor device update its Bluetooth PIN to the PIN included in the request's payload |
| NAME | Request | Requests that the Sensor device update its Bluetooth friendly name to that included in the request payload |
| ADC_GAIN | Request | Requests that the Sensor device change the gain of its ADC to the value contained in the request's payload |
| DAC_LEVEL | Request | Requests that the Sensor device change the output level of its DAC to the value indicated in the request's payload |
| SAMPLE_RATE | Request | Requests that the Sensor device sets the sampling rate of its ADC to the value contained in the request's payload |
| STREAM_START | Request | Requests that the Sensor device starts streaming of GSR samples to the master |
| STREAM_STOP | Request | Requests that the Sensor device stops streaming of GSR samples to the master |
| SAMPLE | Notification | Notifies the master that the payload contains a GSR sample value |
| BATTERY_LOW | Notification | Notifies the master that the Sensor device's battery charge is too low for reliable operation |
| BATTERY_LEVEL | Request | Requests that the Sensor device send a measure of its current battery charge to the master |
| RESET | Request | Requests that the Sensor device reset its mode of operation to a known state |
| POWER_SAVE | Request | Requests that the Sensor device enter power save mode, to prolong battery life |
| POWER_OFF | Request | Requests that the Sensor device powers itself down |
| DEBUG | Notification | Notifies the master that the payload contains debug information |

In addition to the transaction ID's listed in the previous table; the protocol defines the following words:

| Protocol Word | Description |
| --- | --- |
| BEGIN | Signals the beginning of a new transaction message |
| END | Signals the end of the current transaction message |
| ESCAPE | Protects the integrity of the transaction |
| OK | Transaction status - indicates that a request completed successfully |
| ERROR | Transaction status - indicates that a request failed |

All though various specific protocol details are recited herein, any suitable wire-based or wireless protocol can be used to communicate with the biometric devices described herein.

While the invention has been described with reference to illustrative embodiments, it will be understood by those skilled in the art that various other changes, omissions and/or additions may be made and substantial equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

What is claimed is:

1. A system for providing client applications based on biometric data, comprising:

(a) a handheld biometric sensor comprising:
(i) a first electrode and a second electrode, the first and second electrodes sufficiently conductive to transduce electrodermal activity, the first electrode and the second electrode disposed proximate to a housing, and, the first and second electrodes are substantially parallel and face away from each other;
(ii) an amplifier in electrical communication with the first and second electrodes, the amplifier adapted to amplify a transduced electrodermal signal;
(iii) a converter in electrical communication with the amplifier, wherein the converter converts analog electrodermal signals to digital electrodermal data;
(iv) a biometric processor in electrical communication with the converter, the biometric processor capable of controlling a flow of digitized data from the converter, the biometric processor disposed within the housing; and
(v) a wireless link controller, the wireless link controller adapted to wirelessly enable the processor to exchange digital data with a client computing device; and (b) a client computing device comprising:
(i) a wireless link controller, the wireless link controller adapted to wirelessly enable the client computing device to exchange digital data with the biometric processor; and (ii) a client processor for processing digital data provided by the wireless link controller, and running a client application that uses the digital data as input, such that, the client computing device comprises a digital signal analyzer that extracts one or more features from the electrodermal data received from the biometric processor and provides the features to said client application, wherein the digital signal analyzer extracts one or more features from the electrodermal data received from the biometric processor by using a continuous parameter adaptation technique, comprising the steps of:

receiving the electrodermal data from the electrodes over a window of time;

filtering the windowed electrodermal data, wherein the filtering is performed substantially continuously using an adaptive process;

passing the filtered, windowed electrodermal data through a slope calculator;

detecting, if the calculated slope value is positive which indicates a potential stress event and increasing a trend counter accordingly, or, if the calculated slope value is negative and decreasing a trend counter accordingly;

monitoring as to whether the trend counter has increased over or decreased below one or more pre-defined thresholds;

upon the trend counter increasing over one of the pre-defined thresholds, the client computing device altering the system to indicate a higher stress state and the trend counter being reset; and, upon the trend counter decreasing below one of the pre-defined thresholds, the client computing device altering the system to indicate a lower stress state and the trend counter being reset.

2. The system of claim 1 wherein the distance between said first and second electrodes is from about 1 cm to about 4 cm.

3. The system of claim 1 wherein said biometric sensor further comprises a filter that passes more of a phasic component of the electrodermal signal than a tonic component of the electrodermal signal.

4. The system of claim 3 wherein said filter is designed to substantially remove said tonic component, and wherein said processor is programmed to (i) track variations in said tonic component of the electrodermal signal over time, and (ii) provide feedback parameters to said filter to more substantially remove said tonic component.

5. The system of claim 1 wherein said one or more features are selected from the group consisting of a stress level, an anxiety level and a relaxation level.

6. The system of claim 1 wherein said client application is a virtual agent application wherein said features modify the state of a virtual agent causing the behavior of the virtual agent to change.

7. The system of claim 6 wherein said virtual agent is selected from the group consisting of a virtual person, a virtual pet and a virtual plant.

8. The system of claim 1 wherein said digital signal analyzer extracts one or more features from the electrodermal data received from the biometric processor by filtering the electrodermal data to remove high-frequency components; calculating the slope of the filtered data; thresholding the calculated slope values; accumulating a number of events within the thresholded sloped values; and determining the number of accumulated events for a given time period so as to provide these results as features to said client application.

9. The system of claim 1 wherein the system identifies relative stress trends relating to a user's anxiety level.

10. The system of claim 1 wherein the electrodermal data comprises an electrodermal level portion and an electrodermal response portion; and the client processor filters the electrodermal level portion from the electrodermal data.

* * * * *